(12) United States Patent
Mercier et al.

(10) Patent No.: US 10,456,268 B2
(45) Date of Patent: Oct. 29, 2019

(54) SYSTEM OF SPINAL ARTHODESIS IMPLANTS

(71) Applicant: LDR Medical, S.A.S., Sainte-Savine (FR)

(72) Inventors: Alexis Mercier, Verrieres (FR); Samuel Lequette, Pessac (FR)

(73) Assignee: LDR Medical, S.A.S., Sainte-Savine (FR)

( * ) Notice: Subject to any disclaimer, the term of this patent is extended or adjusted under 35 U.S.C. 154(b) by 0 days.

(21) Appl. No.: 15/442,591

(22) Filed: Feb. 24, 2017

(65) Prior Publication Data
US 2017/0246008 A1 Aug. 31, 2017

(30) Foreign Application Priority Data
Feb. 26, 2016 (FR) .................... 16 51637

(51) Int. Cl.
*A61F 2/44* (2006.01)
*A61B 17/88* (2006.01)
(Continued)

(52) U.S. Cl.
CPC ........ *A61F 2/4455* (2013.01); *A61B 17/7064* (2013.01); *A61F 2/442* (2013.01); *A61F 2/4405* (2013.01); *A61F 2/30749* (2013.01); *A61F 2002/305* (2013.01); *A61F 2002/30314* (2013.01); *A61F 2002/30327* (2013.01); *A61F 2002/30492* (2013.01); *A61F 2002/30579* (2013.01); *A61F 2002/30787* (2013.01);
(Continued)

(58) Field of Classification Search
CPC ...... A61F 2/4455; A61F 2/4405; A61F 2/442; A61F 2002/30314; A61F 2002/30327; A61F 2002/30841; A61F 2002/30884

USPC .......... 606/246-249, 75, 301-308, 328, 279; 623/17.11, 17.16
See application file for complete search history.

(56) References Cited

U.S. PATENT DOCUMENTS 5,571,109 A 11/1996 Bertagnoli
5,876,404 A 3/1999 Zucherman et al.
(Continued)

FOREIGN PATENT DOCUMENTS

CA 2868610 10/2013
CN 102525624 7/2012
(Continued)

OTHER PUBLICATIONS

Rajasekaran S, Naresh-Babu J., Translaminar facetal screw (Magerl's) fixation, Dec. 2005, Neurology India, vol. 53, Issue 4, 520.*
(Continued)

*Primary Examiner* — Pedro Philogene
*Assistant Examiner* — David C Comstock
(74) *Attorney, Agent, or Firm* — Schwegman Lundberg & Woessner, P.A.

(57) ABSTRACT

The present invention relates to a spinal arthrodesis system including at least two types of implants from among the three following types:
an intersomatic implant (IS), including at least one passage (40) mating at least one anchoring device (1);
an interspinous implant (IE), including at least two wings able to run along a portion of the vertebral spines (EI, ES);
a facet implant (IF) including a bone attachment.

14 Claims, 14 Drawing Sheets

(51) Int. Cl.
*A61B 17/70* (2006.01)
*A61F 2/30* (2006.01)
(52) U.S. Cl.
CPC .............. *A61F 2002/30841* (2013.01); *A61F 2002/30884* (2013.01); *A61F 2002/448* (2013.01); *A61F 2002/449* (2013.01)

(56) References Cited

U.S. PATENT DOCUMENTS

| | | | |
|---|---|---|---|
| 6,045,579 | A | 4/2000 | Hochshuler et al. |
| 6,447,546 | B1 | 9/2002 | Bramlet et al. |
| 7,291,149 | B1 | 11/2007 | Michelson |
| 7,594,931 | B2 | 9/2009 | Louis et al. |
| 7,682,396 | B2 | 3/2010 | Beaurain et al. |
| 7,695,516 | B2 | 4/2010 | Zeegers |
| 7,842,088 | B2 | 11/2010 | Rashbaum et al. |
| 8,147,556 | B2 | 4/2012 | Louis et al. |
| 8,241,359 | B2 | 8/2012 | Davis et al. |
| 8,257,439 | B2 | 9/2012 | Zeegers |
| 8,267,999 | B2 | 9/2012 | Beaurain et al. |
| 8,343,219 | B2 | 1/2013 | Allain et al. |
| 8,617,245 | B2 | 12/2013 | Brett |
| 8,696,709 | B2 | 4/2014 | Dinville et al. |
| 8,753,397 | B2 | 6/2014 | Beaurain et al. |
| 8,932,359 | B2 | 1/2015 | Brett |
| 8,979,932 | B2 | 3/2015 | Rashbaum et al. |
| 9,039,774 | B2 | 5/2015 | Chataigner et al. |
| 9,044,337 | B2 | 6/2015 | Dinville et al. |
| 9,044,339 | B2 | 6/2015 | Zeegers |
| 9,078,765 | B2 | 7/2015 | Louis et al. |
| 9,101,410 | B1* | 8/2015 | Urrea ................. A61B 17/7064 |
| 9,265,619 | B2 | 2/2016 | Beaurain et al. |
| 9,326,797 | B2 | 5/2016 | Dinville et al. |
| 9,402,658 | B2 | 8/2016 | Dinville et al. |
| 9,463,091 | B2 | 10/2016 | Brett |
| 9,566,164 | B2 | 2/2017 | Zeegers |
| 9,597,194 | B2 | 3/2017 | Rashbaum et al. |
| 9,649,199 | B2 | 5/2017 | Louis et al. |
| 9,713,535 | B2 | 7/2017 | Davis et al. |
| 9,737,412 | B2 | 8/2017 | Brett |
| 9,763,803 | B2 | 9/2017 | Dinville et al. |
| 9,795,485 | B2 | 10/2017 | Allain et al. |
| 9,833,331 | B2 | 12/2017 | Dinville et al. |
| 9,867,716 | B2 | 1/2018 | Zeegers |
| 9,877,842 | B2 | 1/2018 | Chataigner et al. |
| 9,913,667 | B2 | 3/2018 | Dinville et al. |
| 9,925,059 | B2 | 3/2018 | Chataigner et al. |
| 2002/0128712 | A1 | 9/2002 | Michelson |
| 2003/0004572 | A1 | 1/2003 | Goble et al. |
| 2004/0127989 | A1 | 7/2004 | Dooris et al. |
| 2004/0153078 | A1* | 8/2004 | Grinberg ............ A61B 17/8052 606/75 |
| 2005/0055096 | A1 | 3/2005 | Serhan et al. |
| 2005/0096745 | A1 | 5/2005 | Andre et al. |
| 2005/0203512 | A1 | 9/2005 | Hawkins et al. |
| 2005/0234459 | A1 | 10/2005 | Falahee et al. |
| 2006/0079896 | A1 | 4/2006 | Kwak et al. |
| 2006/0235391 | A1* | 10/2006 | Sutterlin, III ....... A61B 17/7064 606/86 A |
| 2006/0271194 | A1 | 11/2006 | Zucherman et al. |
| 2007/0282449 | A1 | 12/2007 | de Villiers et al. |
| 2008/0114456 | A1 | 5/2008 | Dewey et al. |
| 2008/0183209 | A1 | 7/2008 | Robinson et al. |
| 2008/0255622 | A1 | 10/2008 | Mickiewicz et al. |
| 2009/0234389 | A1 | 9/2009 | Chuang et al. |
| 2009/0265007 | A1 | 10/2009 | Colleran |
| 2009/0270929 | A1* | 10/2009 | Suddaby ............ A61B 17/1637 606/324 |
| 2009/0292316 | A1 | 11/2009 | Hess |
| 2010/0087860 | A1* | 4/2010 | Chin ................. A61B 17/1671 606/249 |
| 2010/0106191 | A1 | 4/2010 | Yue et al. |
| 2011/0004247 | A1 | 1/2011 | Lechmann et al. |
| 2011/0040382 | A1 | 2/2011 | Muhanna |
| 2011/0230971 | A1* | 9/2011 | Donner ................. A61B 17/70 623/17.16 |
| 2011/0282459 | A1 | 11/2011 | McClellan, III et al. |
| 2011/0313458 | A1 | 12/2011 | Butler et al. |
| 2012/0010659 | A1 | 1/2012 | Angert et al. |
| 2012/0010662 | A1 | 1/2012 | O'Neil et al. |
| 2012/0184993 | A1* | 7/2012 | Arambula ........... A61B 17/7064 606/246 |
| 2012/0197311 | A1* | 8/2012 | Kirschman ........ A61B 17/7064 606/304 |
| 2012/0215313 | A1 | 8/2012 | Saidha et al. |
| 2012/0232599 | A1 | 9/2012 | Schoenly et al. |
| 2012/0271422 | A1 | 10/2012 | Miller et al. |
| 2013/0018470 | A1 | 1/2013 | Moskowitz et al. |
| 2013/0116732 | A1 | 5/2013 | Pavlov et al. |
| 2013/0226239 | A1* | 8/2013 | Altarac ............. A61B 17/7064 606/247 |
| 2013/0226300 | A1* | 8/2013 | Chataigner ............. A61F 2/442 623/17.16 |
| 2013/0245767 | A1 | 9/2013 | Lee et al. |
| 2014/0025113 | A1 | 1/2014 | McCormack et al. |
| 2014/0052260 | A1 | 2/2014 | McKenny et al. |
| 2015/0051702 | A1 | 2/2015 | Chataigner et al. |
| 2015/0127107 | A1 | 5/2015 | Kim et al. |
| 2015/0142056 | A1* | 5/2015 | Hart .................. A61B 17/7064 606/247 |
| 2015/0250605 | A1 | 9/2015 | Chataigner et al. |
| 2016/0100870 | A1 | 4/2016 | Lavigne et al. |
| 2016/0235547 | A1 | 8/2016 | Beaurain et al. |
| 2016/0317195 | A1 | 11/2016 | Dinville et al. |
| 2017/0224393 | A1 | 8/2017 | Lavigne et al. |
| 2017/0252179 | A1 | 9/2017 | Rashbaum et al. |
| 2017/0319354 | A1 | 11/2017 | Louis et al. |
| 2018/0008430 | A1 | 1/2018 | Davis et al. |
| 2018/0064554 | A1 | 3/2018 | Brett |
| 2018/0092753 | A1 | 4/2018 | Dinville et al. |
| 2018/0104061 | A1 | 4/2018 | Allain et al. |

FOREIGN PATENT DOCUMENTS

| | | |
|---|---|---|
| EP | 2589351 | 5/2013 |
| EP | 3213704 A1 | 9/2017 |
| FR | 2726171 | 5/1996 |
| FR | 2795627 | 1/2001 |
| FR | 2866229 | 8/2005 |
| FR | 2954692 | 7/2011 |
| FR | 3016793 | 7/2015 |
| KR | 20130112407 | 10/2013 |
| KR | 20140018668 | 2/2014 |
| WO | WO0213732 | 2/2002 |
| WO | WO2005091782 | 10/2005 |
| WO | WO2007070819 | 6/2007 |
| WO | WO2007109402 | 9/2007 |
| WO | WO2008149223 | 12/2008 |
| WO | WO2010090801 | 8/2010 |
| WO | WO2010121028 | 10/2010 |
| WO | WO2011019411 | 2/2011 |
| WO | WO2011080535 | 7/2011 |
| WO | WO2011153536 | 12/2011 |
| WO | WO2012030141 | 3/2012 |
| WO | WO2012094647 | 7/2012 |
| WO | WO2012129205 | 9/2012 |
| WO | WO2012154653 | 11/2012 |
| WO | WO2013001097 | 1/2013 |
| WO | WO2013062716 | 5/2013 |
| WO | WO2013072582 | 5/2013 |
| WO | WO2013124453 | 8/2013 |
| WO | WO2013141990 | 9/2013 |
| WO | WO2015164707 | 10/2015 |
| WO | WO2016016474 | 2/2016 |

OTHER PUBLICATIONS

Apparatus and Method for Fusing Opposing Spinal Vertebrae, Bramlet, Dale G. et al., U.S. Appl. No. 09/635,436, filed Aug. 11, 2000.

(56) References Cited

OTHER PUBLICATIONS

Intervertebral nucleus prosthesis and surgical procedure for implanting the same, Gau, Michel, U.S. Appl. No. 10/060,862, filed Jan. 30, 2002.
Intersomatic cage with unified grafts, Huppert, Jean, U.S. Appl. No. 10/276,712, filed Mar. 26, 2003.
Spinal Osteosynthesis Device and Preparation Method, Beaurain, Jacques et al., U.S. Appl. No. 10/473,999, filed Apr. 12, 2004.
Intervertebral Disc Prosthesis and Fitting Tools, Beaurain, Jacques et al., U.S. Appl. No. 10/476,565, filed Jun. 8, 2004.
Vertebral Cage Device With Modular Fixation, Louis, Christian et al., U.S. Appl. No. 10/483,563, filed May 21, 2004.
Progressive approach osteosynthesis device and preassembly method, Delecrin, Joel et al., U.S. Appl. No. 10/492,753, filed Aug. 9, 2004.
Plate for osteosynthesis device and method of preassembling such device, Delecrin, Joel et al., U.S. Appl. No. 10/492,827, filed Jul. 15, 2004.
Osseous anchoring device for a prosthesis, Huppert, Jean et al., U.S. Appl. No. 10/494,418, filed Jul. 22, 2004.
Implant for Osseous Anchoring with Polyaxial Head, Beaurain, Jacques et al., U.S. Appl. No. 10/498,234, filed Dec. 7, 2004.
Intervertebral Disc Prosthesis, Beaurain, Jacques et al., U.S. Appl. No. 10/533,846, filed Nov. 11, 2005.
Osseous anchoring implant with a polyaxial head and method for installing the implant, Renaud, Christian et al., U.S. Appl. No. 10/570,080, filed Jun. 9, 2006.
Device and method for sectioning a vertebral lamina, Mangione, Paolo, U.S. Appl. No. 10/575,065, filed May 30, 2006.
Intervertebral Disc Prosthesis, Hovorka, Istvan et al., U.S. Appl. No. 11/051,710, filed Feb. 4, 2005.
Intervertebral Disc Prosthesis, Zeegers, M. Willem, U.S. Appl. No. 11/098,266, filed Apr. 4, 2005.
Intervertebral Disc Prosthesis, Zeegers, Willem, U.S. Appl. No. 11/109,276, filed Apr. 18, 2005.
Instrumentation and Methods for Inserting an Intervertebral Disc Prosthesis, Dinville, Herve, U.S. Appl. No. 11/180,868, filed Jul. 13, 2005.
Intervertebral Disc Prosthesis, Rashbaum, Ralph et al., U.S. Appl. No. 11/341,007, filed Jan. 27, 2006.
Intervertebral Disc Prosthesis and Instrumentation for Insertion of the Prosthesis Between the Vertebrae, Rashbaum, Ralph et al., U.S. Appl. No. 11/362,253, filed Feb. 24, 2006.
Transforaminal intersomatic cage for an intervertebral fusion graft and an instrument for implanting the cage, Davis, Reginald James et al., U.S. Appl. No. 11/378,165, filed Mar. 17, 2006.
Intervertebral nucleus prosthesis and surgical procedure for implanting the same, Gau, Michel, U.S. Appl. No. 11/390,711, filed Mar. 27, 2006.
Intervertebral disc prosthesis insertion assemblies, Jodaitis, Alexandre et al., U.S. Appl. No. 11/676,237, filed Feb. 16, 2007.
Intersomatic cage with unified grafts, Huppert, Jean, U.S. Appl. No. 11/767,386, filed Jun. 22, 2007.
Nucleus Prostheses, Vila, Thierry et al., U.S. Appl. No. 11/874,144, filed Oct. 17, 2007.
Vertebral Support Device, Cho, Paul et al., U.S. Appl. No. 11/958,285, filed Dec. 17, 2007.
Intervertebral disc prosthesis, surgical methods, and fitting tools, Beaurain, Jacques et al., U.S. Appl. No. 12/025,677, filed Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Cho, Paul, U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, Willem, U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Interveterbral disc prosthesis insertion assemblies, Jodaitis, Alexandre et al., U.S. Appl. No. 12/527,373, filed Mar. 19, 2010.
Intervertebral implant having extendable bone fixation members, Brett, Darrell C., U.S. Appl. No. 12/884,664, filed Sep. 17, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Hervé et al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., U.S. Appl. No. 13/454,927, filed Apr. 24, 2012.
Anchoring Device and System for an Intervertebral Implant, Intervertebral Implant and Implantation Instrument, Dinville, Hervé et al., U.S. Appl. No. 13/520,041, filed Nov. 26, 2012.
Anchoring Device and System for an Intervertebral Implant, Intervertebral Implant and Implantation Instrument, Dinville, Hervé et al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, Willem, U.S. Appl. No. 13/603,043, filed Sep. 4, 2012.
Intervertebral Disc Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervé et al., U.S. Appl. No. 13/774,547, filed Feb. 22, 2013.
Transforaminal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Inserting an Intervertebral Disc Prosthesis, Dinville, Herve, U.S. Appl. No. 13/892,933, filed May 13, 2013.
Intervertebral Disc Prosthesis Insertion Assemblies, Jodaitis, Alexandre et al., U.S. Appl. No. 13/919,704, filed Jun. 17, 2013.
Intervertebral implant having extendable bone fixation members, Brett, Darrell C., U.S. Appl. No. 14/064,434, filed Oct. 28, 2013.
Interspinous Implant and Instrument for Implanting an Interspinous Implant, Dinville, Hervé et al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prosthesis, Vila, Thierry et al., U.S. Appl. No. 14/159,161, filed Jan. 20, 2014.
Interveterbral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al., U.S. Appl. No. 14/246,442, filed Apr. 7, 2014.

(56) References Cited

OTHER PUBLICATIONS

Interspinous Implant and Instrument for Implanting an Interspinous Implant, Dinville, Hervé et al., U.S. Appl. No. 14/252,754, filed Apr. 14, 2014.
Anchoring device for a spinal implant, spinal implant and implantation instrumentation, Chataigner, Hervé et al., U.S. Appl. No. 14/252,852, filed Apr. 15, 2014.
Intervertebral Disc Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Steib, Jean-Paul, U.S. Appl. No. 14/325,317, filed Jul. 7, 2014.
Anchoring device and system for an intervertebral implant, intervertebral implant and implantation instrument, Chataigner, Hervé et al., U.S. Appl. No. 14/380,714, filed Aug. 23, 2014.
Cage Having Spike, Kim, Seo-Kon et al., U.S. Appl. No. 14/460,536, filed Aug. 15, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis, Hovorka, Istvan et al., U.S. Appl. No. 14/513,818, filed Oct. 14, 2014.
Plate for osteosynthesis device and preassembly method, Delecrin, Joel et al., U.S. Appl. No. 14/584,674, filed Dec. 29, 2014.
Intervertebral Implant Having Extendable Bone Fixation Members, Brett, Darrell C., U.S. Appl. No. 14/594,770, filed Jan. 12, 2015.
Vertebral implant, device for vertebral attachment of the implant and instrumentation for implantation thereof, Ameil, Marc et al., U.S. Appl. No. 14/638,746, filed Mar. 4, 2015.
Intervertebral Disc Prosthesis, Zeegers, Willem, U.S. Appl. No. 14/642,696, filed Mar. 9, 2015.
Vertebral Support Device, Cho, Paul et al., U.S. Appl. No. 14/642,752, filed Mar. 10, 2015.
Intervertebral Disc Prosthesis, Rashbaum, Ralph et al., U.S. Appl. No. 14/659,587, filed Mar. 16, 2015.
Anchoring device and system for an intervertebral implant, intervertebral implant and implantation instrument, Chataigner, Hervé et al., U.S. Appl. No. 14/721,818, filed May 26, 2015.
Intervertebral Disc Prosthesis, Zeegers, Willem, U.S. Appl. No. 14/726,557, filed May 31, 2015.
Anchoring Device and System for an Intervertebral Implant, Intervertebral Implant and Implantation Instrument, Dinville, Hervé et al., U.S. Appl. No. 14/726,558, filed May 31, 2015.
Vertebral Cage Device With Modular Fixation, Louis, Christian et al., U.S. Appl. No. 14/798,900, filed Jul. 14, 2015.
Bone Implants, Lavigne, Christophe et al., U.S. Appl. No. 14/815,900, filed Jul. 31, 2015.
Devices, Methods, and Systems to Implant and Secure a Fusion Cage or Intervertebral Prosthesis for Spinal Treatment, Stewart, Will et al., U.S. Appl. No. 14/827,297, filed Aug. 15, 2015.
Vertebral implant, vertebral fastening device of the implant and implant instrumentation, Dinville, Hervé et al., U.S. Appl. No. 14/891,322, filed Nov. 13, 2015.
Instruments and Methods for Removing Fixation Devices from Intervertebral Implants, Dinville, Herve et al., U.S. Appl. No. 14/931,007, filed Nov. 3, 2015.
Instrumentation and Methods for Inserting an Intervertebral Disc Prosthesis, Dinville, Herve, U.S. Appl. No. 15/012,815, filed Feb. 1, 2016.
Intervertebral Disc Prosthesis, Beaurain, Jacques et al., U.S. Appl. No. 15/049,934, filed Feb. 22, 2016.
Intervertebral Disc Prosthesis and Instrumentation for Insertion of the Prosthesis Between the Vertebrae, Steib, Jean-Paul, U.S. Appl. No. 15/049,995, filed Feb. 22, 2016.
Anchoring device for a spinal implant, spinal implant and implantation instrumentation, Chataigner, Hervé et al., U.S. Appl. No. 15/115,659, filed Jul. 29, 2016.
Interspinous Implant and Implantation Instrument, Dinville, Hervé et al., U.S. Appl. No. 15/145,413, filed May 3, 2016.
Implant for Osseous Anchoring with Polyaxial Head, Beaurain, Jacques et al., U.S. Appl. No. 15/145,431, filed May 3, 2016.
Intervertebral disc prosthesis, surgical methods, and fitting tools, Beaurain, Jacques et al., U.S. Appl. No. 15/150,316, filed May 9, 2016.
Interspinous Implant and Instrument for Implanting an Interspinous Implant, Dinville, Hervé et al., U.S. Appl. No. 15/225,612, filed Aug. 1, 2016.
Intervertebral Disc Prosthesis, Zeegers, M. Willem, U.S. Appl. No. 15/269,923, filed Sep. 19, 2016.
Intervertebral Implant Having Extendable Bone Fixation Members, Brett, Darrell C., U.S. Appl. No. 15/289,861, filed Oct. 10, 2016.
Vertebral implant, device for vertebral attachment of the implant and instrumentation for implantation thereof, Ameil, Marc et al., U.S. Appl. No. 15/309,197, filed Nov. 6, 2016.
Intervertebral Disc Prosthesis Insertion Assemblies, Jodaitis, Alexandre et al., U.S. Appl. No. 15/340,565, filed Nov. 1, 2016.
Nucleus Prosthesis, Vila, Thierry et al., U.S. Appl. No. 15/391,305, filed Dec. 27, 2016.
Plate for osteosynthesis device and preassembly method, Delecrin, Joel et al., U.S. Appl. No. 15/414,523, filed Jan. 24, 2017.
Implant for Osseous Anchoring with Polyaxial Head, Beaurain, Jacques et al., U.S. Appl. No. 15/426,938, filed Feb. 7, 2017.
Intervertebral Disc Prosthesis, Zeegers, Willem, U.S. Appl. No. 15/432,795, filed Feb. 14, 2017.
System of spinal arthodesis implants, Mercier, Alexis et al., U.S. Appl. No. 15/442,591, filed Feb. 24, 2017.
Intervertebral Disc Prosthesis, Rashbaum, Ralph et al., U.S. Appl. No. 15/464,639, filed Mar. 21, 2017.
Transforaminal intersomatic cage for an intervertebral fusion graft and an instrument for implanting the cage, Davis, Reginald James et al., U.S. Appl. No. 15/465,143, filed Mar. 21, 2017.
Bone Implants, Lavigne, Christophe et al., U.S. Appl. No. 15/501,166, filed Feb. 1, 2017.
Bone anchoring system, associated implant and instrumentation, Lequette, Samuel et al., U.S. Appl. No. 15/582,568, filed Apr. 28, 2017.
Vertebral System, Implant and Inserts for Vertebral System, Joly, Florian et al., U.S. Appl. No. 15/586,003, filed May 3, 2017.
Vertebral Cage Device With Modular Fixation, Louis, Christian et al., U.S. Appl. No. 15/597,130, filed May 16, 2017.
Intervertebral Disc Prosthesis, Hovorka, Istvan et al., U.S. Appl. No. 15/603,429, filed May 23, 2017.
Transforaminal intersomatic cage for an intervertebral fusion graft and an instrument for implanting the cage, Davis, Reginald James et al., U.S. Appl. No. 15/659,602, filed Jul. 25, 2017.
Vertebral Support Device, Cho, Paul et al., U.S. Appl. No. 15/677,310, filed Aug. 15, 2017.
Intervertebral Implant Having Extendable Bone Fixation Members, Brett, Darrell C., U.S. Appl. No. 15/682,549, filed Aug. 22, 2017.
Anchoring Device and System for an Intervertebral Implant, Intervertebral Implant and Implantation Instrument, Dinville, Hervé et al., U.S. Appl. No. 15/708,860, filed Sep. 19, 2017.
Spinal Osteosynthesis Device and Preparation Method, Beaurain, Jacques et al., U.S. Appl. No. 15/708,907, filed Sep. 19, 2017.
Cage Having Spike, Kim, Seo-Kon et al., U.S. Appl. No. 15/723,174, filed Oct. 3, 2017.
Devices, Methods and Systems to Implant and Secure an Intervertebral Implant for Spinal Treatment, Stewart, Will et al., U.S. Appl. No. 15/753,168, filed Feb. 15, 2018.
Intervertebral disc prosthesis, surgical methods, and fitting tools, Beaurain, Jacques et al., U.S. Appl. No. 15/784,559, filed Oct. 16, 2017.
Intersomatic cage, intervertebral prosthesis, anchoring device and implantation instruments, Allain, Jerome et al., U.S. Appl. No. 15/792,123, filed Oct. 24, 2017.
Expansible Intervertebral Implant, Bernard, Pierre et al., U.S. Appl. No. 15/796,732, filed Oct. 27, 2017.
Expansible Intersomatic Cage, Bernard, Pierre et al., U.S. Appl. No. 15/796,733, filed Oct. 27, 2017.
Expansible Intersomatic Cage, Bernard, Pierre et al., U.S. Appl. No. 15/796,735, filed Oct. 27, 2017.

(56) References Cited

OTHER PUBLICATIONS

Anchoring Device and System for an Intervertebral Implant, Intervertebral Implant and Implantation Instrument, Dinville, Hervé et al., U.S. Appl. No. 15/832,101, filed Dec. 5, 2017.
Intervertebral Disc Prosthesis, Zeegers, Willem, U.S. Appl. No. 15/872,937, filed Jan. 16, 2018.
Anchoring device for a spinal implant, spinal implant and implantation instrumentation, Chataigner, Hervé et al., U.S. Appl. No. 15/883,199, filed Jan. 30, 2018.
Intervertebral Disc Prosthesis, Zeegers, M. Willem, U.S. Appl. No. 15/895,463, filed Feb. 13, 2018.
Interspinous Implant and Instrument for Implanting an Interspinous Implant, Dinville, Hervé et al., U.S. Appl. No. 15/919,220, filed Mar. 13, 2018.
Anchoring device for a spinal implant, spinal implant and implantation instrumentation, Chataigner, Hervé et al., U.S. Appl. No. 15/937,845, filed Mar. 27, 2018.
Vertebral implant, vertebral fastening device of the implant and implant instrumentation, Dinville, Hervé et al., U.S. Appl. No. 15/949,292, filed Apr. 10, 2018.
Implant for Osseous Anchoring with Polyaxial Head, Beaurain, Jacques et al., U.S. Appl. No. 15/955,643, filed Apr. 17, 2018.
Intervertebral Fusion Cage with Retractable-Extrudable Pins, Brett, Darrell C., U.S. Appl. No. 61/243,297, filed Sep. 17, 2009.
Intervertebral Fusion Cage with Retractable-Extrudable Pins, Brett, Darrell C., U.S. Appl. No. 61/260,364, filed Nov. 11, 2009.
National Institute of Industrial Property (France); Search Report in Fench Pub. No. FR3048176, App. No. FR1651637; dated Dec. 5, 2016; National Institute of Industrial Property (France); France; all pages.
European Patent Office; Search Report in EP Pub. No. EP3213704, App. No. EP17158258; dated Aug. 7, 2017; European Patent Office; Germany; all pages.

* cited by examiner

Fig. 14A
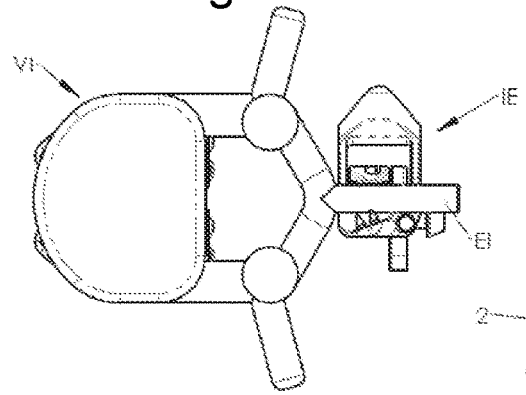
Fig. 14B
Fig. 14C
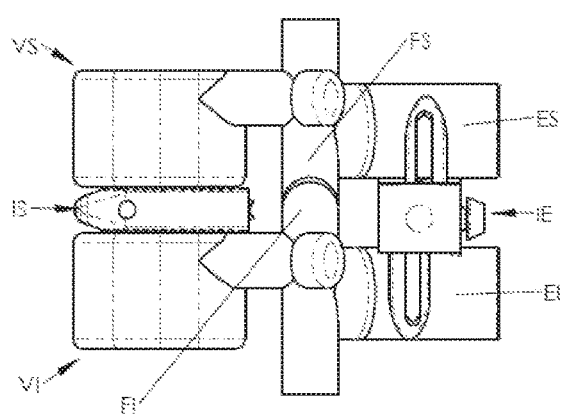
Fig. 14D
Fig. 14E
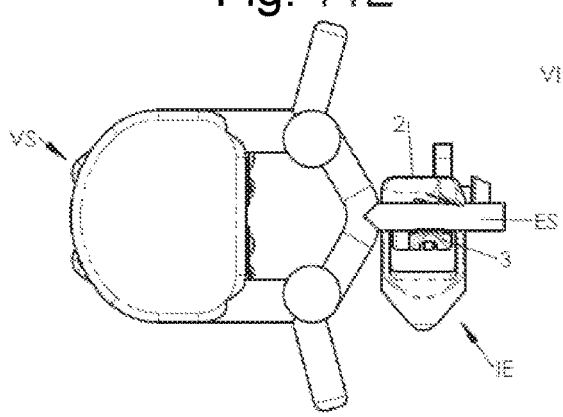

SYSTEM OF SPINAL ARTHODESIS IMPLANTS

CROSS-REFERENCE TO RELATED APPLICATIONS

Priority is claimed under 35 U.S.C. § 119 to French Patent Application No. FR1651637 filed in FRANCE on Feb. 26, 2016, which is incorporated herein for all purposes.

BACKGROUND

The present invention relates to the field of spinal implants, in particular for arthrodesis of at least two vertebral structures. The present invention more particularly relates to a system of spinal implants intended to ensure fusion of at least two adjacent vertebrae (i.e. arthrodesis).

A problem in the field of implants relates to bone growth and notably arthrodesis, i.e. the bone fusion of two structures, such as for example vertebrae. Indeed, sometimes a fusion of at least two vertebrae is sought to be obtained, for example when at least one of their adjacent intervertebral discs is lesioned. From the prior art various arthrodesis techniques are known, based on diverse types of implants, such as for example intersomatic (or arthrodesis) cages inserted in the place of a disc for promoting bone growth, or arthrodesis plate attached on two vertebrae for immobilizing them and allowing arthrodesis, or further osteosynthesis or arthrodesis bars, used for immobilizing the vertebrae, to which they are generally connected by pedicular screws or hooks, or finally interspinous implants inserted between the spines of the vertebrae (or "spinous processes") for immobilizing them and thus facilitating fusion. The bars or plates are generally used as an addition to intersomatic cages which allow extended fusion since it is located at the vertebral bodies. This additional use results from a problem known in the field which is to stabilize the vertebral level to be treated. It is also known, notably at the lumbar and sacral level, of solutions using facet implants (interfacet or transfacet implants) allowing attachment of the articular facets with the purpose of obtaining fusion.

Generally, these solutions aim at further solving the problem of the stability of the implant and of the treated vertebral structures. It is necessary that an implant be stable in its implantation site, in particular when arthrodesis is desired since the latter should take place in a relative position of the rachis elements which is optimum (as desired by the surgeon). Stabilization and/or a locking of the implant are therefore often preferable. Various solutions of the prior art therefore aim at providing stable arthrodesis implants.

Thus, it has been suggested in the prior art that it would be desirable to use implants which are complementary with each other, such as for example osteosynthesis bars or plates in combination with intersomatic cages. Further, the fact that the rachis has actually three major stability axes has been suggested in the literature, notably by F. Denis in his/her article "The Three Column Spine and Its Significance in the Classification of Acute Thoracolumbar Spinal Injuries" in the journal SPINE 1983. Vol. 8, no. 8, pp 817-831, but also by R. Louis in his/her article "Spinal stability as defined by the three-column spine concept" in the journal Anatomia Clinica, 1985 Vol. 7, pp 33-42, and then by R. Roy-Camille in his/her article "L'instabilité Rachidienne/Spinal Instability" in the journal Rachis, 1994, Vol. 6, no. 2 pp 107-112 and more recently by Sabina MARCOVSCHI CHAMPAIN, in her thesis for obtaining the Doctoral degree of the l'École Nationale Supérieure d'Arts et Métiers, specialization "Biomechanics" at the l'École doctorale no. 432 (Sciences des Métiers de l'Ingénieur), document no. 2008/ENAM-0024.

However, most solutions of the prior art do not give the possibility of benefiting from these teachings of the literature and of proposing a stable spinal arthrodesis system, notably because of the general problems of the ease and/or rapidity of the implantation and of the invasivity of the implants and of surgical techniques which depend thereon. Indeed, it is generally desired that the implants be able to be rapidly and/or easily implanted with minimum invasivity, i.e. it is sought to limit the size of the incisions and damages on the surrounding tissues. This invasivity problem in particular relates to the introduction of the implants into the spine and notably the access to the intervertebral spaces (disc spaces) which is often particularly delicate because of the congestion, for example because of the presence of blood vessels and nerves near the intervertebral space, as well of the proximity of the spinal cord. The implants and their bone anchoring devices have to penetrate sufficiently deeply into the vertebrae for ensuring good attachment. As regards the implantation, various approach routes for placing the implant are possible, even if a given route is generally preferred for each of the various spinal stages, sometimes because of the preference and facility of the surgeon for this route, but also because of the pathology to be treated (a hernia may be rather posterior, therefore easier to withdraw through a posterior route), but further because of the anatomy of the patient (vessels in the axis of the anterior approach route or too prominent muscles, etc). For example (in a non-limiting way), a median anterior mini-invasive approach (MIS, "Mini-Invasive Spine Surgery") approach may be preferred for cervical vertebrae and a lateral or anterolateral mini-invasive approach for thoracic or lumbar vertebrae. In particular, certain implants (notably intersomatic cages), generally at the lumbar level are provided so as to be implanted through a posterior route (from the rear of the patient) or a transforaminal route (through the foramen). The posterior route generally requires resection (generally partial resection) of the articular and/or facets and passes between the dura mater and the articulars (generally two cages are provided each positioned on one side of the sagittal plane). This route therefore follows a path very close to the spinal cord. The transforaminal route follows an oblique route relatively to the sagittal plane and requires cages with a sufficient length so as to be positioned obliquely or perpendicularly to the sagittal plane. Access routes as small as possible are generally sought in order to limit invasivity of the implantation surgical operation. Thus, in order to obtain an implant as less invasive as possible (i.e., not requiring the clearing of a wide approach route), it is necessary to reduce the size of the implant and ideally to limit the size of the passage required both for implantation and for attachment of the implant. Indeed, the implants which are anchored in vertebrae often add an additional constraint on the size and invasivity.

It will be noted that the invasivity problem provides additional constraints for meeting the stability problem, notably because the fact of reducing the dimensions for reducing the invasivity is accompanied with risks of instability. It is therefore interesting to propose a solution which allows reconciliation of the constraints related to invasivity and stability.

In this context, it is interesting to propose a solution giving the possibility of effectively tackling at least one portion of these problems.

BRIEF SUMMARY

The object of the present invention is to overcome certain drawbacks of the prior art by proposing a combination of bone implants, in particular intended for implantation via a mini-invasive approach (MIS) in the discal space between the adjacent vertebrae, further allowing stable, easy, rapid implantation and with reduced invasivity.

This object is achieved by a spinal arthrodesis system comprising several implants of several types, for the arthrodesis of at least two adjacent vertebrae, characterized in that it includes on the one hand:

- at least one intersomatic implant, intended to be implanted in the discal space between said adjacent vertebrae for maintaining a distance between each other and including at least one bone anchoring device for anchoring said intersomatic implant in at least one of said vertebrae, and, on the other hand, at least one implant from among both following types of implants:
- at least one implant of the interspinous type implant, intended to be implanted between two vertical spines of said adjacent vertebrae, the interspinous implant including at least two wings of dimensions arranged so as to be inserted between both spines, from one of their side faces;
- at least one implant of the facet type, intended to be implanted between and/or through the articular facets of the vertebrae and formed with an elongated body along a longitudinal axis and provided with a head and turns of at least one threading, over at least one portion in proximity to the free end, said body including at least one longitudinal internal conduit, over at least one portion along the longitudinal axis, and/or windows crossing said body transversely to the longitudinal axis and/or stabilization means at the head in order to be supported on the surrounding bone tissues.

This type of solution, using a combination of several implants of several types, which are not very invasive and easy to implant, further has the advantage of providing a more extensive and more reliable arthrodesis by the accumulated and synergistic effect of the different types of implants used. Indeed, this combination made possible by the technical characteristics of small size and low invasivity of the implants, gives the possibility of immobilizing at least two of the three great stability axes of the rachis, and thus obtain a more rapid and more reliable arthrodesis than with the implants used independently of each other. Finally, in order to optimize arthrodesis and reduce the invasivity of the implants, said implants are configured so as to be able to be implanted through an access route through the less invasive access route to the vertebrae, i.e. through a posterior or transforaminal insertion route, at least at the lumbar level.

According to another particularity, said system for arthrodesis of at least two adjacent vertebrae, comprises at least one intersomatic implant and at least one interspinous implant.

According to another embodiment, said system for arthrodesis of at least two adjacent vertebrae, comprises at least one intersomatic implant and at least one facet implant.

According to another particularity, said system comprises a posterior intersomatic implant. A posterior intersomatic implant meaning that said implant is intended to be inserted into the discal space between both adjacent vertebrae, through a posterior approach or route.

According to another particularity, said system comprises an intersomatic transforaminal implant. A transforaminal intersomatic implant meaning that said implant is intended to be inserted in the discal space between both adjacent vertebrae, through a transforaminal approach or route.

According to another embodiment, the intersomatic implant has an elongated and curved profile for assuming for example the shape of a banana or a half banana.

According to another particularity, said intersomatic implant includes at least one peripheral wall, for which at least one portion, a so-called posterior portion, including at least one passage, complementary dimensions and orientations to the shapes and dimensions of said anchoring device including at least one rigid and elongated body along a longitudinal axis extending between a first end, a so-called anterior end, and a second end, a so-called posterior end, said body being inserted without any deformation into said passage, substantially in the plane of the intersomatic implant, by sliding from said posterior portion of the intersomatic implant, said passage crossing the intersomatic implant from the periphery to an upper or lower surface so that the anterior end of said body penetrates into one of said adjacent vertebrae, while the posterior end remains in said passage and retains said intersomatic implant against said vertebra.

According to another particularity, said body of the anchoring device is curved.

According to another particularity, said body of the anchoring device is curved so as to be able to penetrate into one of the adjacent vertebrae by being introduced into the intersomatic implant along an approach axis substantially in the same plane as that of the intersomatic implant.

According to another particularity, at least one of the upper and lower surfaces of the peripheral wall includes notches avoiding displacement of the intersomatic implant between the vertebrae between which it is intended to be implanted.

According to another particularity, said body of the anchoring device includes at least one rib or second plate cooperating with at least one groove made in the passage of the implant.

According to another particularity, said posterior end of said body of the anchoring device includes at least one abutment pressing the intersomatic implant against said vertebra.

According to another particularity, said body of the anchoring device includes at least one abutment opposing the withdrawal of said anchoring device of the intersomatic implant.

According to another particularity, said posterior end of said body of the anchoring device includes at least one abutment oriented non-parallel to the longitudinal axis of the body and complementary of at least one abutment of at least one locking device of the device with respect to the intersomatic implant, said locking means which equips the implant being provided with at least one flexible portion allowing, on the one hand, the pushing back of said abutment of the locking means in order to insert the anchoring device in the passage, and on the other hand, mutual engagement of both abutments when they are found facing each other, by the elastic return of the flexible portion.

According to another particularity, the peripheral wall of the intersomatic implant includes at least one attachment means intended to cooperate with a gripping end of implantation instrumentation.

According to another particularity, the median planes passing through the upper and lower surfaces of the intersomatic implant form an angle oriented along an anteroposterior axis of the intersomatic implant giving the possibility of imposing a lordosis or a kyphosis to the vertebrae between which the intersomatic implant is intended to be implanted.

According to another particularity, the median planes passing through the upper and lower surfaces of the intersomatic implant are substantially parallel with each other.

According to another particularity, the peripheral wall includes two passages each oriented towards one of the upper and lower surfaces, so as to allow the anchoring of the anchoring device in each of the adjacent vertebrae between which the intersomatic implant is intended to be implanted.

According to another particularity, the peripheral wall includes at least one chamfer on at least one peripheral portion of at least one of its upper and lower surfaces, so as to facilitate insertion of the intersomatic implant between the vertebrae.

According to another particularity, said interspinous implant comprises means for immobilizing at least one of the spines between which it is intended to be implanted.

According to another particularity, said immobilization means are attachment or anchoring means in at least one of the spines.

According to another particularity, said immobilization means are hooking-up means for at least one of the spines.

According to another particularity, said immobilization means are means for compressing at least one of the spines.

According to another particularity, the interspinous implant includes two wings on the one hand, each positioned on a side face of the implant opposite to the other wing and each protruding towards one of the two spines, so that the wings each run along a spine but on opposite side faces, and at least one passage crossing said body from one side face to the other on the other hand and receiving at least one means for retaining the interspinous implant, formed by an insert, inserted from the same side face of the implant, the insert being of a substantially sigmoidal shape by the fact that its forms a wing including at least two radii of curvature with opposite orientations, so that both faces of the wing each include a concave portion and a convex portion, the passage and the insert being laid out so that when the insert (is housed in the passage at least one portion of said convex portions of both faces of the insert each run along at least one portion of the spines, on side faces opposite to those bordered by the wings.

According to another particularity, said compression means for compressing the side faces of the spinous processes between said wings of said insert when the latter is inserted through said passage of the interspinous implant.

According to another particularity, the compression means are formed by two curved wings of the inserts connected through an articulation axis allowing the deployment of both wings from a folded position upon inserting the insert into the passage at a deployed position wherein said wings compress the spinous processes against the wings of the implant.

According to another particularity, the insert of the interspinous implant is retained in the body by at least one abutment mechanism.

According to another particularity, the interspinous implant includes, on the side opposite to the one provided with both wings, at least one chamfer facilitating the insertion of the implant between the two adjacent spines.

According to another particularity, the interspinous implant includes at least one spinous hooking-up means laid out for being hooked up around at least one portion of the edges of the spines, which are opposite to the edges of the spines between which the body of the implant is inserted.

According to another particularity, said internal conduit of the facet implant is obtained by at least one first central machining parallel to the longitudinal axis and said windows of the facet implant are obtained by at least a second machining in a plane, a so-called transverse plane, not parallel to the longitudinal axis, so that said windows preserve at least one portion of said turns and the wall of the body behind the turns, and preserve non-machined portions on the periphery of said body of the facet implant.

According to another particularity, said windows of the facet implant include at least one sharpened outer side edge.

According to another particularity, said free end of the body of the facet implant is self-drilling.

According to another particularity, at least one portion of said body of the facet implant is substantially cylindrical or conical or frustoconical.

According to another particularity, the periphery of said threading is substantially cylindrical in spite of the cylindrical or conical or frustoconical shape of the body of the facet implant.

According to another particularity, said windows are aligned with each other along the longitudinal axis.

According to another particularity, said windows are shifted relatively to each other along the longitudinal axis.

According to another particularity, said head of the implant closes the longitudinal internal conduit or includes means for closing the longitudinal internal conduit.

According to another particularity, said thread has a variable pitch which shortens towards the head.

According to another particularity, said body is provided with several threads of different pitches, the pitch of a thread located on the side of the free end being of a larger size than the adjacent thread located on the side of the head.

According to another particularity, said head of the facet implant is provided with means for stabilizing the implant, intended to be supported on the bone tissue around said head.

According to another particularity, said stabilization means include at least one stabilization element comprising at least two rods having a pointed free end and substantially parallel to the longitudinal axis and able to penetrate the tissue around the head and optionally of a portion of said body of the facet implant in proximity to said head.

According to another particularity, said rods are connected together with a ring making the stabilization element capable of being mounted on said head.

According to another particularity, said stabilization means include at least one stabilization element with the shape of a bell mounted on the head and the periphery of which is intended to be supported on the bone tissue surrounding the head.

According to another particularity, said bell includes at least one spike or tooth on its periphery for facilitating bone anchoring.

According to another particularity, said bell is mounted and secured to the head.

According to another particularity, said head has a peripheral lower surface with the shape of a sphere portion and mating an internal upper surface of said bell thereby jointed on the head of the implant.

According to another particularity, said stabilization means include locking means pressing on the stabilization element in order to maintain it pressed against the bone tissue.

According to another particularity, at least one portion of said windows are separated by at least two turns without windows.

According to another particularity, at least one portion of said windows are made on several turns.

Other particularities and advantages of the present invention are detailed in the following description.

BRIEF DESCRIPTION OF THE SEVERAL VIEWS OF THE DRAWING

Other particularities and advantages of the present invention will become more clearly apparent upon reading the description hereafter, made with reference to the appended drawings, wherein:

FIGS. 2E and 2F represent a profile view of an anchoring device of the anchor type of an intersomatic implant according to another embodiment;

FIGS. 14A, 14B, 14C, 14D and 14E represent respectively underside, front perspective, profile, rear perspective and top views of an arthrodesis system according to an embodiment comprising an intersomatic implant and an interspinous implant, for the arthrodesis of two adjacent vertebrae, at least one of which is visible in each of these figures.

DETAILED DESCRIPTION OF VARIOUS EMBODIMENTS

Figure 1A:
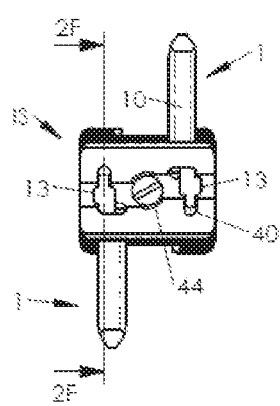
FIGS. 1A, 1B, 1C and 1F represent respectively rear, profile, perspective and sectional views along the plane 2F-2F of FIG. 1A, of an intersomatic implant provided with an anchoring device of the anchor type according to an embodiment.

The present invention relates to a system for arthrodesis (bone fusion) of at least two adjacent vertebrae. Such a system includes at least two implants of at least two different types. The present invention thus for example relates to a spinal arthrodesis system including at least two types of implants from among the three following types:

An intersomatic implant (IS),
An interspinous implant (IE),
A facet implant (IF).

More particularly, a system will generally be selected, the implants of which have technical features giving the possibility of meeting at least one portion of the problems mentioned in the present application.

Thus, diverse embodiments relate to a spinal arthrodesis system comprising several implants of several types, for the arthrodesis of at least two adjacent vertebrae (VI, VS), characterized in that it includes on the one hand:

at least one intersomatic implant (IS), intended to be implanted in the discal space between said adjacent vertebrae (VI, VS) for maintaining a distance between them and including at least one bone anchoring device for anchoring said intersomatic implant (IS) in at least one of said vertebrae (VI, VS) and, on the other hand, at least one implant from among the two following types of implants:

at least one implant of the interspinous type (IE), intended to be implanted between two vertebral spines (EI, ES) of said adjacent vertebrae (VI, VS), the interspinous implant (IE) including at least two wings (21, 22, 31, 33) able to each run along at least one portion of at least one side face of at least one of said spines (EI, ES);

at least one implant of the facet type (IF) elongated along a longitudinal axis between a free end and a head (78) and intended to be implanted between and/or through the articular facets of the vertebrae (VI, VS), said implant of the facet type (IF) comprising at least one wedge provided with a bone attachment or only at least one bone attachment, said wedge and/or said bone attachment including at least one longitudinal internal conduit (71) in at least one portion along the longitudinal axis, and/or windows (75) crossing said wedge and/or said bone attachment transversely to the longitudinal axis and/or stabilization means at the head (78) for being supported on the surrounding bone tissues.

Preferably, said bone attachment of the facet implant (IF) is:

either formed with a rigid, preferably curved anchor, for example similar to the bone anchoring device (1) of the intersomatic implant (IS), but with reduced dimensions for a use in articular facets;

or formed with a screw provided with turns (72) of at least one threading, on at least one portion in proximity to the free end.

Further, said interspinous implant (IE) generally comprises means for immobilizing at least one of the spines (EI, ES) between which it is intended to be implanted. Diverse examples and advantages of such immobilization means are described hereafter.

Preferably, said intersomatic implant (IS) is configured for implantation in the discal space between said adjacent vertebrae (VI, VS), through a mini-invasive approach (MIS), for example by passing through the same cut as the other type of implant (or via small cuts close to each other, but preferably limiting the restricted lesions of the underlying tissues during the passage of the implants). Implants with a small size are generally preferred for avoiding the endangering of the blood vessels and the surrounding nerve tissues, and it is often preferred that the implants be anchored by means of bone anchoring devices which should penetrate sufficiently deeply into the vertebrae in order to ensure good attachment and give the possibility of obtaining a stable implant. A not very invasive implant will for example be defined by the fact that it (and/or its attachment) does not require more space (or little space) near the intervertebral space when necessary for introducing the actual spinal implant.

Access routes as small as possible are generally preferred for limiting the invasivity of the implantation surgical operation. Therefore, in order to obtain an implant as less invasive as possible not requiring the clearance of a wide approach route, it is necessary to reduce the size of the implant and to limit the size of the passage for the implantation and attachment. Thus, an intersomatic implant (IS) is generally preferred, configured for an implantation from the rear face of the vertebral column, i.e. along dorsal (or posterior) or transforaminal approaches, well known to one skilled in the art.

Thus, with at least such an intersomatic implant (IS) combined with at least one interspinous implant (IE) and/or at least one facet implant (IF), it is possible to provide a not very invasive system providing vertebral stabilization in several points and allowing rapid and reliable arthrodesis, while reducing the duration of the operation required for the implantation. Indeed such a system gives the possibility of surmounting the incompatibility which existed up till now between, on the one hand, the fact of implanting several implants during a surgical intervention and, on the other hand the fact of remaining as less invasive as possible and as rapid as possible. Further, such a system immobilizes the vertebrae in several points and gives the possibility of avoiding that bone fusion occurs in a relative position of the vertebrae which is not the desired one during the implantation. Indeed, because of the movements of the patients while the arthrodesis is in progress, there exists a risk that the vertebrae slightly move relatively to each other, resulting in a bone fusion in an undesired position or even in a non-fusion. It is for this reason that in the prior art stabilization bars attached by pedicular screws were often used, while they are very invasive and difficult to implant, unlike various embodiments of the present invention.

The use of anchored intersomatic implants in the vertebrae and combined with at least one other implant located on the other side of the medullar canal therefore provides an equivalent system in stability, while providing the many advantages detailed below. The diverse embodiments of the system therefore allow stabilization in two or three points (vertebral body, facets, spine) which allows a good distribution of the loads and forces, in addition to allowing in the long run a fusion in one or two points (vertebral body, facets), or even in three points but the fusion of the spines is generally not provided. In the various embodiments shown in the present application, an intersomatic implant of the "posterior" or "transforaminal" type are therefore preferred (these implants being often called intersomatic or intervertebral cages or arthrodesis cages). One skilled in the art, notably surgeons, are well aware of the various types of intersomatic implants and will appreciate the technical characteristics which result from these terms, from among which mention may be made, as a non-limiting example, a relatively elongated shape (for the posteriors), sometimes curved (for the transforaminal). Thus, in various preferred embodiments of the invention, the intersomatic implant (IS) has dimensions making it able for one of the posterior or transforaminal approaches. For a lumbar intersomatic implant (IS), both of these approaches will be preferred by means of the synergy of the combined implants (IS, IE, IF) in the system, as detailed above. For example, for a posterior implant, the height of the implant (i.e. its dimension along the vertical axis of the rachis once it is implanted) may at the posterior level (i.e., towards the dorsal face of the patient) be of the order of 5 mm, but may range up to a value of about 20 mm, generally less from 10 to 16 mm. The height at the anterior level (i.e. towards the ventral face of the patient) will generally be comprised between 10 mm and 16 mm but may range up to a value of about 20 mm. These dimensions are generally adjusted depending on the vertebral stage and on the pathology and are adjusted as a function of each other for adjusting lordosis provided by the implant. The width of the posterior intersomatic implant (IS) will generally be substantially constant over the whole of its depth (or length), even if slight variations in shapes are often provided for making the implant more streamlined, for example in order to provide better penetration. This width at the moment of the insertion of the implant in its passage for a passing of the implant through the posterior route will be less than 20 mm and generally preferably less than 15 mm in order to avoid damaging the spinal cord and/or the nerve roots. Finally, the depth (or length, but the term of depth is more suitable since the dimension in which the implant is driven-in in the distal space) is designated here will generally be comprised between 18 mm and 38 mm, preferably between 24 mm and 27 mm. As regards the transforaminal intersomatic implant (IS), preferred for a transforaminal lumbar intervertebral fusion (TLIF), the width will generally be also substantially constant over the whole of its depth (or length) even if slight variations in shapes are often provided and especially frequent curving of the implant in this direction, so that it may be positioned in an optimum way in the discal space. This width will generally be less than 15 mm but this type of implant may sometimes be wider since the approach to the vertebrae along this route is sometimes less delicate than through the posterior route. In the same way as for the posterior implants, the height or the heights of the transforaminal implant, at the anterior and posterior levels, will be selected depended on the configuration of the vertebrae and on the possible desired lordosis, in the same values of less than 20 mm, with the particular difference that the oblique orientation of the implant imposes that the angle formed between the upper and lower surfaces is made in an adequate way for the final orientation of the implant in the discal space. On the other hand, this oblique orientation allows this type of transforaminal implant to be longer than the posterior implant and therefore has a depth comprised between 25 mm and 40 mm, preferably between 30 mm and 35 mm.

One skilled in the art will therefore easily understand that he/she may easily and rapidly implant this type of intersomatic implant (patient in the "ventral decubitus" position, without it being necessary to turn it over during the intervention) at the same time as at least one facet implant and/or one interspinous implant, by limiting the lesions of the patient and he/she will easily estimate the localization and the extension (limited) of the incision(s) which he/she may carry out for such a combined implantation of the system.

In certain embodiments, the spinal arthrodesis system, comprising several implants of several types, for the arthrodesis of at least adjacent two vertebrae (VI, VS) is characterized in that it includes on the one hand:
- at least one transforaminal or posterior intersomatic implant (IS) intended to be implanted in the discal space between said adjacent vertebrae (VI, VS) for maintaining a distance between them and including at least one bone anchoring device (1) for anchoring said intersomatic implant (IS) in at least one of said vertebrae (VI, VS) and, on the other hand, at least one implant from both types of the following implants:
- at least one implant of the interspinous type (IE) intended to be implanted between two vertebral spines (EI, ES) of said adjacent vertebrae (VI, VS), the interspinous implant (IE) including at least two wings and preferably means for immobilizing the vertebral spines (EI, ES);
- at least one implant of the facet type (IF) elongated along a longitudinal axis between a free end and a head (78) and intended to be implanted between and/or through the articular facets of the vertebrae (VI, VS), said implant of the facet type (IF) comprising at least one wedge provided with a bone attachment or only at least one bone attachment, said wedge and/or said bone attachment including at least one longitudinal internal conduit (71) in at least one portion along the longitudinal axis, and/or windows (75) crossing said wedge and/or said bone attachment transversely to the longitudinal axis and/or stabilization means at the head (78) for being supported on the surrounding bone tissues.

According to diverse embodiments, said immobilization means are means for attaching or anchoring in at least one of the vertebral spines (EI, ES) and/or means for hooking-up at least one of the vertebral spines (EI, ES) and/or means for compressing at least one of the vertebral spines (EI, ES).

Preferably, said bone attachment of the facet implant (IF) in this system using at least one posterior or transforaminal intersomatic (IS) implant is:
- either formed by a rigid anchor, preferably a curved anchor, for example similar to the bone anchoring device (1) of the intersomatic implant (IS), but with reduced dimensions for use in articular facets;
- or formed by a screw provided with turns (72) of at least one threading, on at least one portion in proximity to the free end.

Generally, facet implants are wedges or screws and in the present application, one benefits from the bone attachment by the screw (alone or associated with a wedge). The present application therefore preferentially describes facet screws, with a threaded body (80) and a head (78), but it is understood that this example cannot be considered as being limiting.

A main object of the present invention is to produce stable and rapid bone fusion, while limiting the invasivity of the implantation. The stability of the fusion is ensured by the use of a system comprising a combination of at least two types of implants from among the different types of intersomatic (IS), interspinous (IE) and facet implants (IF) described in the present application. The different types of implant of the system are configured for an implantation in the discal space between said vertebrae, (VI, VS) by a mini-invasive approach (MIS). The implantation by an MIS approach gives the possibility of inserting one or several of said implants through a surgical approach damaging as less as possible the tissues of the patient, by means of a reduction of the number of incisions and/or of the size of the incision and/or of the extension of the ablations or resections for example. Thus, said arthrodesis system has the advantage of using a combination of implants selected for their stabilities and for the possible synergistic effects between them since their combined use gives the possibility of obtaining an arthrodesis with a greater stability than the one obtained by each implant used alone. Further, the selection of the implants combined in various embodiments of the system gives the possibility on the one hand of obtaining an invasivity less than the one of other combinations of implants and, on the other hand an easier and rapid implantation than with other combinations of implants. Indeed, these synergies are in particular obtained in various embodiments of the invention by imposing implantation characteristics via a posterior or transforaminal route for the intersomatic implant, preferably provides with vertebral anchoring, in combination with an interspinous implant with deployable wings which may therefore be inserted between the spines from only one of their side faces and/or with a facet implant which is generally rapidly screwed between or through articular facets. Thus, by an approach from the dorsal face of the patient, along the spinous processes, optionally through a single incision (or a single incision on each side of the spinous processes), the surgeon may achieve arthrodesis with all the advantages detailed above.

The different configurations of the arthrodesis system:

In certain embodiments, the system includes at least one implant of the intersomatic type (IS), preferably anchored in at least one of said vertebrae (VI, VS), but ideally anchored in these two adjacent vertebrae (VI, VS). Further, this intersomatic implant (IS) is preferably combined with an implant of the interspinous type (IE) and/or with at least one facet implant (IF). It will be noted that the expression "at least one" used in the present application for intersomatic (IS) and facet (IF) implants in fact often designates only the alternatives of a single implant or of two implants, since it is seldom that one uses more than two copies of the implants since rarely more than one on each side of the sagittal plane (or of a parasagittal plane) are implanted. Nevertheless, only because it is possible to desire treating several vertebral stages at the same time, this expression should not be interpreted as only designating both of these sole alternatives.

Figure 11:
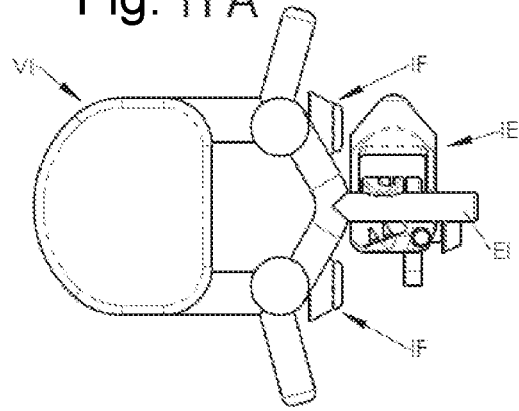
FIGS. 11A, 11B, 11C, 11D and 11E represent respectively underside, front perspective, profile, rear perspective and top views, of an arthrodesis system according to an embodiment comprising an intersomatic implant, and interspinous implant and two facet implants for the arthrodesis of two adjacent vertebrae, at least one of which is visible in each of these figures.
Figure 11:
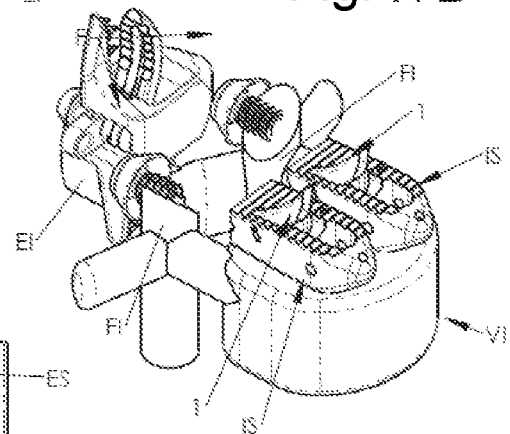
Figure 11:
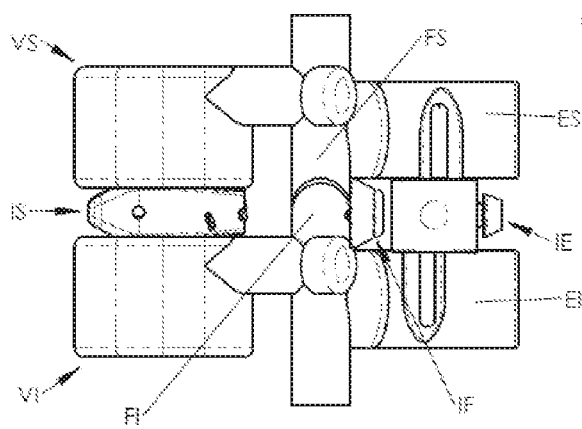
Figure 11:
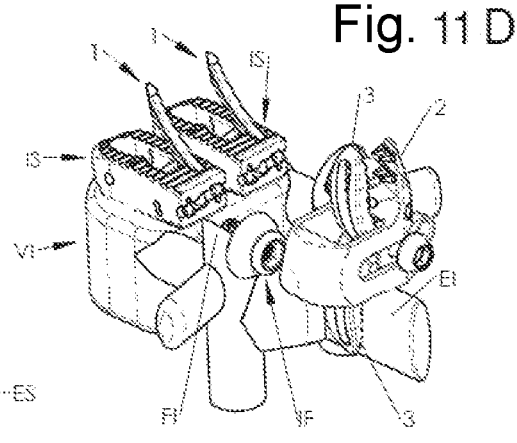
Figure 11:
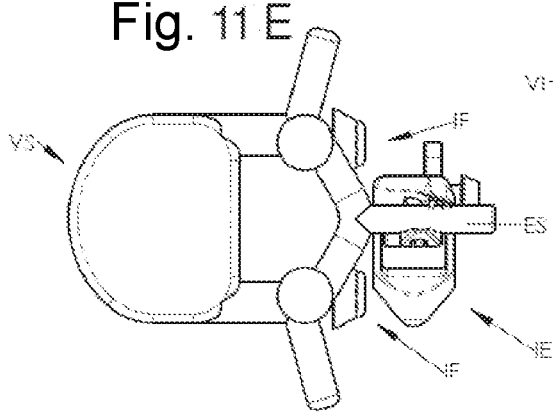

FIGS. 5 to 14 show illustrative and non-limiting examples of diverse possible configurations of the system, i.e. of usable combinations of implants. The particular implants illustrated in each of these combinations should not be interpreted as being limiting, as detailed in the present application and the combinations of implants are actually those which are detailed hereafter: FIG. 5 (A to D) shows an exemplary configuration comprising two facet implants (IF) and an intersomatic implant (IS). The intersomatic implant (IS) is an implant of the transforaminal type in FIGS. 5 (B to D). FIGS. 7 (A to D), 9 (A to D) and 10 (A to E) show exemplary configurations comprising two facet implants (IF) and two intersomatic implants (IS). The intersomatic implants (IS) are implants of the posterior type, with substantially parallel positioning, in FIGS. 9 (B to D) and 10 (B to D), and of the posterior type with oblique positioning or of the transforaminal type in FIG. 7 (B to E). FIGS. 8 (A to E) show exemplary configurations comprising two intersomatic implants (IS) and an interspinous implant (IE). The intersomatic implants (IS) are implants of the posterior type, with substantially parallel positioning, in these figures but it is possible to provide instead a posterior type with oblique positioning or a transforaminal (not shown) type. FIGS. 11 (A to E) show exemplary configurations comprising two facet implants (IF), an interspinous implant (IE) and two intersomatic implants (IS). The intersomatic implant (IS) is a posterior implant (as for example the one of FIGS. 8, 9 and 10), also it is possible to replace it with an intersomatic implant (IS) of the posterior type (with parallel or oblique positioning). This penultimate possibility is moreover is all the more realistic since, by having implanted two intersomatic implants, the implantation of a second facet implant would generally not require any additional incision. On the other hand, according to the required ablations or resections (which depends on the particular configuration of the rachis of the patient), it is sometimes not possible to preserve the facets of both sides and one may therefore be led to only using a single facet implant, even if two intersomatic implants have been used would have been made as a posterior one and would not add any extension. FIGS. 6 (A to D) show examples of such a system with a single facet implant, in this case combined with a single intersomatic implant, which is of the transforaminal type.

FIGS. 13A to 13D show exemplary configurations comprising two intersomatic implants and two facet implants. FIGS. 14A to 14E show exemplary configurations comprising two intersomatic implants and one interspinous implant. In these examples, the intersomatic implant is of the posterior type and comprises an anchoring device of the screw type; on the contrary to the anchoring device of the intersomatic implants of the other figures which is of the anchor type, except for FIGS. 2A to 2D. It will be noted that this type of configuration is particularly advantageous since it achieves a majority of the goals sought by the invention. Indeed, this configuration allows efficient and rapid vertebral stabilization since said configuration gives the possibility of increasing the area of the discal space stabilized by two not very invasive implants, while allowing easy and rapid implantation by the surgeon. Indeed, this type of configuration gives the possibility of minimizing the invasivity of the surgical intervention since the surgeon may limit himself/herself to a single incision, generally a median incision, most often in the sagittal plane at the spinous processes, in order to be able to implant both posterior intersomatic implants through the two posterior approach routes located on either side of the spinous processes. The surgeon may of course make a partial resection of the bone structures for letting through the intersomatic implants, the dimensions of which may therefore vary, notably in the value range detailed in the present application. Advantageously, the surgeon may pass by the same incision for then implanting at least one facet implant and/or at least one interspinous implant (on at least one vertebral stage). Thus, this configuration gives the possibility of efficiently and rapidly implanting two to five implants through a single incision and thus obtain an unbeatable vertebral stabilization in such a short time. Thus, the invention may also relate to a method for arthrodesis of at least two adjacent vertebrae (VI, VS), typically comprising a median incision at at least one dorsal spine (EI, ES), sometimes followed by partial resection of the basal articulars or laminars or of other bone structures for inserting both posterior intersomatic implants. It will be noted that during this type of intervention, the surgeon may prefer to make a partial resection of the spinous processes in order to facilitate the insertion of the implants, by suppressing the supraspinatus ligament and a portion of the free end of the spinous process. In this case, it is understood that it is no longer necessary to use an interspinous implant which is capable of being inserted from a single side face of the spinous processes (which aims at preserving the supraspinatus ligament and the spines) since it becomes easier to lay the interspinous implant by translation parallel to the sagittal plane. Thus, the invention may therefore relate to the use of a combination of at least one posterior intersomatic implant with at least one interspinous implant comprising set wings (non-deployable). Indeed, the interspinous implant is then not limited to the types of interspinous implants described in detail in the present application, but the system may also comprise other types of interspinous implants with mobile or set elements of the prior art (including certain types of interspinous implants with mobile or set elements of the state of the art which are described above), such as for example the implants of the prior art U.S. Pat. No. 5,876,404 and US 2005/203512. Thus, in certain cases of partial resection of the spinous processes, less advantageous implants than most of the interspinous implants described in the present application may also be implanted. On the other hand, as the invention is directed to good stabilization of the rachis with view to arthrodesis, it will be preferred that the intersomatic implant includes means for immobilizing the spinous processes, for example such as hooking-up means or compression means for the spinous processes or further attachment means anchored in the spinous processes, including illustrative and non-limiting examples described in the present application. The method therefore includes, subsequently to the step for inserting at least one intersomatic implant, a step for anchoring this implant via the posterior approach used for its implantation. These steps may be repeated on the other side for inserting a second intersomatic implant through the same posterior route and anchoring of this implant. Nevertheless, it is possible to only use one single posterior intersomatic implant, notably if the method provides oblique orientation in the discal space or if this implant is of the expansible type in the plane of the discal space, in order to increase the area stabilized by the implant. Indeed, posterior intersomatic implants are known which are expansible and preferably anchoring of the latter will be provided for use in a system according to the present invention. Next, the method may finally include the introduction of at least one facet implant (interfacet or transfacet) and/or the introduction of the interspinous implant.

Generally, a particularity of the arthrodesis system according to various embodiments is that it is generally preferred that at least two of the implants used be anchored in bone structures. In particular, an anchored intersomatic implant is preferred, i.e. attached solidly, preferably in both vertebral plates (a plate of each of the adjacent vertebrae). Also, the transfacet implants form a bone anchoring and diverse interfacet implants also have a bone anchoring or a stabilization (and they generally allow finally fusion of the articulars). Finally, in the case of an interspinous implant, it is preferred that it includes means for immobilizing the spinous processes, so as to prevent torsion and/or flexure movements of the patient, in addition to the extension which is naturally limited by the presence of the implant between the spinous processes if the dimensions are determined properly. Thus, generally, the use of an intersomatic implant will be preferred, which immobilizes the vertebral bodies with a facet implant and/or an interspinous implant which also gives the possibility of immobilizing the vertebral structure in which they are implanted, so as to obtain immobilization in several points and achieve most of the objects that the present invention aims at solving. In particular, it is with this type of synergistic immobilization or attachment of several spinal implants that various embodiments of the invention give the possibility of limiting the risks for the patient while meeting a maximum of goals, notably in terms of surgical intervention time, invasivity and stability and/or reliability.

Finally, it will be noted that in the examples of FIGS. 10 (A to E), the facet implants used are implants of the transfacet type, i.e. they are implanted through facets of both adjacent vertebrae, while in the other figures, the facet implants used are implants of the interfacet type, i.e. they are implanted between the facets of two adjacent vertebrae. Of course, transfacet or interfacet implants may generally be used in any of the combinations detailed previously. It is moreover possible to also use an interfacet implant on one side with a transfacet implant on the other side, while the somatic implants will generally be the same when there are two of them.

According to a preferred embodiment of the present invention, said system is intended for arthrodesis of at least two lumbar vertebrae (VI, VS) and preferring an implantation of said implants for bone fusion via a mini-invasive approach, preferably a transforaminal approach or a posterior approach. More specifically, said arthrodesis system is intended for a posterior lumbar intervertebral fusion (Posterior Lumbar Interbody Fusion PLIF) or a transforaminal lumbar intervertebral fusion (Transforaminal Lumbar Interbody Fusion TLIF).

The various implants used in a system according to various embodiments of the invention may be different from those illustrated in the figures of the present application and assume highly varied shapes, notably such as those of the many known intersomatic (IS), interspinous (IE) and facet (IF) implants of the prior art.

The different types of implants of the arthrodesis system:

Here one refers to several implants and to several types of implants since the present application describes a system comprising a combination of several types of implants and may, for each type of implant use several implants. For example, it is possible to use two facet implants in combination with two intersomatic implants and thereby obtain a system comprising four implants, but only two types of implants. Further, it will be noted that it is possible to use for example several types (at least two) of implants and several implants of each type, but the implants of a given type (intersomatic, interspinous or facet) may not be identical with each other. Thus, the present application provides a use of the implants detailed further on in combination with each other, but also in combination with other implants (for example known from the prior art), but preferably implants having the same stability and/or invasivity advantages as those detailed in the present description.

In certain embodiments, the system includes implants such as those illustrated in the figures of the present application, so as to optimize the synergistic effects between the implants and provide the advantages described in detail in the present application. Generally, in these preferred embodiments, the spinal arthrodesis system therefore more specifically comprises at least one implant of the intersomatic type (IS) for example of the type of those illustrated in a non-limiting way in FIGS. 1 (A, B, C, E and F) and 2 (A, B, C and D) on the one hand, and at least one implant of the interspinous type (IE) for example of the type illustrated in a non-limiting way in FIGS. 3 (A, B, C and E) and/or at least one implant of the facet type (IF) for example such as those illustrated in a non-limiting way in FIGS. 4 (A, B, D and E) and 12 (A to D), on the other hand.

Various embodiments will now be described with reference to the figures of the present application, in order to illustrate in more detail the preferred characteristics for the various types of implants.

The anchoring devices (1) (or "anchoring system" or "attachment devices" or "screws" or further "anchors") of the intersomatic implants (IS) may be used in combination with each other or in combination with other types of attachment devices and/or intersomatic implants, of the present application or of the prior art. Indeed, it is possible to use for example those described in the following applications, the mentioned figures and the corresponding passages of their description are incorporated by reference into the present application: EP 2 688 521 (FIGS. 1 and 5, page 7—line 9 to page 8—line 5 and page 8—line 9 to 11), WO 2010/121028 (FIGS. 1 and 9, paragraphs [74] to [76] and [104]), WO 2002/013732 (FIGS. 1 to 4, page 4—lines 7 to 20), WO 2013/141990 (FIGS. 3, 4 and 7, page 7—line 8 to page 8—line 10), WO 2012/094647 (FIGS. 1 and 2, paragraph [23]), WO 2013/072582 (FIGS. 3, 4 and 11, page 10—line 11 to page 11—line 1), WO 2011/153536 (FIGS. 1, 2 and 4, paragraphs [27] and [35]), WO 2010/090801 (FIGS. 1, 2, 7 and 8, paragraph [54]), FR 2 795 627 (FIGS. 1 to 4, page 3—line 28 to page 29—line 11), US 2014/052260 (FIG. 1, paragraph [32]), WO 2013/062716 (FIGS. 1 to 8, paragraphs [5] and [34]), WO 2011/019411 (FIG. 1, paragraph [33]), US 2009/265007 (FIGS. 4 to 7, paragraph [23]), CN102525624 (FIGS. 1 to 7), US 2015/0127107 (FIGS. 1 to 3, paragraph [38]), KR20140018668 (FIGS. 1 and 2), WO 2015/164707 (FIGS. 1, 3 and 5, paragraphs [8] and [55]), U.S. Pat. No. 5,571,109 (FIG. 1), US 2005/096745 (FIG. 1, paragraph [3]), US 2011/282459 (FIGS. 1 and 2 paragraph [9]), US 2012/0271422 (FIGS. 1, 13 and 16), US 2012/0215313 (FIGS. 1 and 2, paragraph [41]), US 2007/0282449 (FIGS. 1, 5 and 6) and US 2002/0128712 (FIGS. 1 and 4, paragraph [36]). It will be noted that the use of devices will be preferred which give the possibility of meeting the invasivity problem in a similar way to those of the present application, i.e. by means of an attachment achieved by an approach in the same plane as the insertion plane of the implant. Thus, the use of anchoring systems including several anchoring devices (1) is provided, which may either be identical or different, or even mating with each other. The intersomatic implants (IS) are preferably laid out so as to receive one or several of such anchoring devices or systems (1), and include in a non-exclusive way, intersomatic cages (IS) configured for an implantation via a posterior or transforaminal route, as described in the present application, even if it is sometimes possible to use other implants intended for other approach routes. The posterior intersomatic implants (IS), preferably anchored, are preferably of the type of those described in the present application but it is possible to use other types of interspinous implants, such as for example as described in the following applications, the mentioned figures of which and the corresponding passages of their description are incorporated by reference to the present application: FR 3 016 793, FR 2 954 692, US 2013/245767 (FIGS. 2 to 4 and 7, paragraphs [16], [18] and [42]), US 2011/0040382 (FIGS. 1 and 2, paragraphs [9], [80] and [105]), FR 2 866 229 (FIG. 1) and U.S. Pat. No. 6,045,579 (FIGS. 4 and 5). The transforaminal intersomatic implants (IS), preferably anchored, are preferably of the type of those described in the present application but it is possible to use other types of interspinous implants, such as for example as described in the following applications, the mentioned figures of which and the corresponding passages of their description are incorporated by reference to the present application: FR 3 016 793, FR 2 954 692, US 2013/018470 (FIGS. 1 and 2, paragraph [69]) and FR 2 866 229 (FIGS. 1 and 5).

The interspinous implants (IE) are preferably of the type of those described in the present application but it is possible to use other types of interspinous implants, such as for example as described in the following applications, the mentioned figures of which and the corresponding passages of their description are incorporated by reference to the present application: US 2009/292316 (FIGS. 1 and 2, paragraphs [10] and [51]), U.S. Pat. No. 5,876,404 (FIGS. 21 and 22, page 1—lines 29 to 43 and page 7—lines 24 to 36), US 2010/106191 (FIGS. 3 and 4; paragraphs [09] and [31], US 2008/114456 (FIG. 3, paragraphs [06] and [66]), US 2005/203512 (FIGS. 1, 4 and 6, paragraph [55]), WO 2007/109402 (FIGS. 2 and 7, page 2—lines 1 to 12), WO 2007/70819 (FIGS. 4 and 17, page 2—line 28 to page 3—line 2), US 2006/271194 (FIG. 1, paragraph [51]), US 2011/0313458 (FIGS. 1 and 9, paragraphs [11], [12] and [15]), US 2009/0234389 (FIGS. 2 and 3, paragraphs [5] and [13]), WO 2012/30141 (FIGS. 1 and 2) and KR20130112407 (FIGS. 1 and 2). It will be noted that interspinous implants will preferably be used, giving the possibility of meeting the invasivity problem in a similar way to those of the present application, i.e. by means of an implantation from a single side face of the spines by limiting the lesions of the inter-spinous and supraspinatus ligaments.

Also, the facet implants (IF) are preferably of the type described in the present application but it is possible to use other types of facet implants since this type of implants generally requires being simply placed between the articular surfaces or through the latter, without requiring a wide approach route to the articular surfaces. Thus, it is for example possible to use facet implants of the type of those described in the following applications, the mentioned figures of which and the corresponding passages of their description are incorporated by reference to the present application: US 2012/010662 (FIGS. 1, 4 and 5, paragraphs [62] and [81]), EP 2 589 351 (FIGS. 6 and 19, paragraphs [3] and [93]), EP 1 718 228 (FIGS. 3 to 5, paragraphs [2] and [14]), U.S. Pat. No. 7,291,149 (FIGS. 1 to 3 and 12, page—lines 20 to 35 and page 4—line 56 to page 5—line 2), US 2012/010659 (FIGS. 2 and 3, paragraph [119] and [121]), US 2011/004247 (FIG. 2, paragraph [5]), US 2013/116732 (FIGS. 1 and 2, paragraphs [14], [15] and [37]), US 2008/255622 (FIG. 2, paragraph [8]), US 2012/0232599 (FIG. 1, paragraphs [5] and [52]), US 2014/025113 (FIG. 2, paragraph [47]), CA2868610 (FIG. 1, page 12—line 13 to page 13—line 12), US 2005/234459 (FIG. 2, paragraphs [4] and [42]), and WO 2012/154653 (FIGS. 2, 6 and 21, paragraphs [3] and [25]). However, the implants described here are preferred for their solidity and/or for the stability and reliability of articular fusion.

Each of these types of implants (objects or groups of objects) may include various possible embodiments, relative to a given object. Each of the objects includes various elements (generally constitutive of the object) characterized by at least one technical characteristic. Each relevant object (from a given group) with at least one technical characteristic may be associated with at least one other object (of the same or of another group), for example with respect to at least one additional technical characteristic, so that the object groups share a common inventive concept. The present application may therefore relate to an assembly comprising at least two of these objects. The various elements (for example, a body, a plate, an abutment, a stop, a chamfer or bevel, etc) as well as their technical characteristics (for example, a curvature, an orientation, a length, a width, a height, a shape, a dimension etc) are described with more details hereafter in the present application. At least one technical characteristic (or combination of characteristics), for example corresponding to an element of a given object, generally solves at least one technical problem, in particular from among those mentioned in the preamble of the present application. The present application therefore describes various embodiments or configurations for each object or group of objects, by specifying at least one technical characteristic of at least one element. It will be understood upon reading the present application that each of the technical characteristics of each element, described in at least one embodiment or a configuration, may be isolated from the other characteristics of the relevant object (or of the relevant and/or associated objects) by said embodiment or said configuration (and therefore relating to the same element or a different element) and/or may be combined with any other technical characteristic described here, in various embodiments or configurations, unless if the opposite has been explicitly mentioned, or if these characteristics are incompatible with each other and/or their combination does not work. Indeed, the structural adaptations which may in particular be required by such isolations or combinations of characteristics may be directly derived from the appreciation of the operating considerations provided in the present application. Also, although certain technical characteristics are discussed here with reference to the anchoring device, they may be incorporated into various embodiments of configurations of the anchoring systems. Generally, the specific technical characteristic(s) relating to a given element should not be considered as exclusive from those relating to another element, or other technical characteristics relating to the same, except if it appears clearly that the combination is impossible or non-functional. Although the present application details various embodiments or configurations of the invention (including preferred embodiments), its spirit and its scope should not be limited to the given examples.

Implants of the Intersomatic Type (IS):

Various embodiments of the intersomatic implant (IS) according to the present invention may be used for the arthrodesis of at least two adjacent vertebrae (VI, VS), as illustrated in a non-limiting way in FIGS. 1A to 1F and 2A to 2F.

In various embodiments, the use of intersomatic implants provided with bone anchoring is preferred. Nevertheless, because of the bulkiness, the anchoring will preferably be selected from anchoring devices in the form of a curved anchor since it allows implantation of the anchor through an approach which is substantially in the plane of the distal space. Thus, intersomatic implants (IS) are for example used, intended to be implanted in the discal space between the adjacent vertebrae (VI, VS) and including at least one peripheral wall for which at least one portion, a so-called posterior portion, includes at least one rectilinear-shaped passage (40) with dimensions and orientation mating the shapes and dimensions of at least one anchoring device or anchor or screw (1) including at least one rigid and elongated body (10) along a longitudinal axis extending between one first end, a so-called anterior end, and a second end a so-called posterior end, said body (10) being inserted without any deformation into said passage (40), substantially in the plane of the intersomatic implant (IS), by sliding from said posterior portion of the intersomatic implant (IS), said passage (40) crossing the intersomatic implant (IS) from the periphery to an upper or lower surface so that the anterior end of said body (10) penetrates into one of said adjacent vertebrae (VI, VS), while the posterior end remains in said passage (40) and retains said intersomatic implant (IS) against said vertebra (VI, VS).

The terms of "to anchor or anchoring" are defined in the present application, as a solid and sufficiently deep implantation in the vertebral plates for ensuring a good hold of the implant flattened against these vertebrae, as opposed to simple anti-skid teeth frequently used which moreover one generally finds under the reference (42) of the present application. An anchored implant, according to definition of the present application, typically includes at least one anchoring device, such as a screw or an anchor, the latter being preferably and generally formed by a curved and rigid plate. The rigidity of this type of anchor allows efficient attachment, generally more efficient than staples or other thin and/or relatively flexible devices, or even fragile. Thus, this type of solution includes an anchoring device of an intervertebral implant in vertebrae, including a body comprising at least one curved and elongated plate along a longitudinal axis, the anchoring device being intended to be inserted through a passage crossing at least one portion of the implant, so that the anterior end of the anchoring device penetrates the bone tissue, while the posterior end of the anchoring device remains in the implant for retaining it.

In certain embodiments, alternatively, the intersomatic implant (IS) may be attached against the vertebrae by means of at least one vertebral anchoring screw known from the prior art, generally used with a screwdriver with a universal joint because of the congestion, even if at least one anchor (1) as described above and below is preferably generally used.

Said anchoring device (1) is intended to be anchored in one of the vertebrae so as to attach the implant on/against this vertebra. Various embodiments of anchoring devices (1) according to the invention include at least one rigid and elongated body (10) preferably curved and with the shape of a plate or nail (with a rectangular, circular, square, polygonal or T-shaped, L-shaped, U-shaped or even H-shaped section), laid down so as to penetrate into a vertebra through at least one implant for retaining this implant against this vertebra. The anchoring device (1) of an intervertebral intersomatic implant (IS) in the vertebrae is sometimes designated in the present application under the term of "anchor" (1) with reference to its anchoring function, without inducing any limitation. Various embodiments of anchors have been described in the published applications WO 2008/149223, WO 2011/080535 and WO 2013/124453 filed by the applicant of the present application, but also in other unpublished applications, the present application provides embodiments which improve the solutions provided by these applications and more easily applied to any implant, in particular spinal implant (spinal being used here as identical with rachis or vertebral) but optionally with other applications. Thus, the present invention provides improvement of various structures and methods which may be used in diverse applications for reducing the invasivity of the operations required for implantation of the implant and of the anchor and for improving the reliability of the proposed solutions.

The term of "rigid" is therefore used here for specifying that it is preferred that the anchor (1) passes through the implant (IS) without having to undergo any elastic deformation or any deformation. Further, by this it is meant that it may provide rigidity and sufficient solidity for withstanding the stresses which will be exerted on it, without deforming or at the very least without deforming in a too substantial way. The passage (40) in the implant (IS) may then, in order to receive this anchor (1), preferably a curved anchor, but it may be rectilinear from the moment when its dimensions are adapted to those of the anchor and to the radius (ii) of curvature of the latter.

In diverse embodiments, the anchor (1) includes a body comprising at least one body (10), preferably rigid, elongated along a longitudinal axis. This longitudinal axis of the anchor (1) extends between a first end, designated here as an "anterior end", intended to penetrate into a vertebrae and a second end, designated here as a "posterior end". It will be noted that the designations of the "posterior" and "anterior" ends of the anchor (1) and of the implant (IS) are used in the present application with reference to the direction along which the anchor (1) is inserted. Thus, for the anchor (1), the first end, a so-called anterior end, is the one intended to be inserted first and intended to penetrate into a vertebra for attaching an implant. As regards the intersomatic implant, its wall or its end designated as posterior is the one including an opening of a passage (40) for inserting the anchor (1), whether this wall is actually posterior to the implant or not during its deployment. In the case of intersomatic cages (IS) or prosthesis of disc or plates described in the present application, this posterior end may actually be positioned towards the rear of the patient or not, notably for the cages which are essentially intended for an implantation via a posterior or transforaminal route.

Certain embodiments of intersomatic implants relating to an intersomatic cage which are laid out for insertion in the discal space via a transforaminal route and the posterior end will therefore be positioned on a lateral and rear side of the vertebrae when the anterior end will be positioned in proximity to the opposite front and lateral side. Nevertheless, the terms of "anterior" and "posterior" are all the same used here since they are easier to understand from a point of view of the implantation and may be used practically and commonly with the anchor (1) and with the implant (IS), regardless of the selected implantation route. Therefore, the terms of "anterior" and "posterior" are not intended to simply refer to the patient or to one of his/her anatomic characteristics, but to the direction of insertion of the anchor into the implant (whether this implant is itself implanted along an anteroposterior axis or not). On the other hand, by the terms of "height" and "thickness" are generally meant here the dimensions of the elements along an orientation parallel to the axis of the rachis (once they are implanted therein) and the terms of "upper" and "lower" (or above and below) are generally also defined according to this orientation (vertical when the patient is standing), without any limiting implication for the invention. Also, the terms of "vertical" and "horizontal" are used in a non-limiting way with reference to the axis of the rachis when considering the standing patient. On the other hand, by the terms of "width" and "length" are meant dimensions along a plane perpendicular to the axis of the rachis (a transverse plane), with the width being generally in the medio-lateral direction while the length is in the anteroposterior direction, without this conventional definition having at the very least any limiting implication for the invention. Also it will be noted that reference is made here to a longitudinal axis between two ends and that this longitudinal axis possibly corresponds to an anteroposterior axis of the anchor (1), but that this axis is in fact oblique generally since the anchor is often inserted from the periphery of the rachis into a vertebral structure (most often a vertebral body and generally in a vertebral plate). Further, this axis of the anchor even follows a curved path in many embodiments and is therefore designated as being anteroposterior with respect to the ends of the anchor rather than with reference to the rachis. Also, the axis of the passage is designated by using the same references when it is oblique and it may be curvilinear or rectilinear. It will also be noted that this definition is also extended to the implant (IS) always with reference to the direction of insertion of the anchor (1). It will be also noted that the term of "significantly" or "substantially" is regularly used in the present description, notably relating to a characteristics such as an orientation or a direction, so as to indicate that the relevant characteristic may in fact be slightly different and not be exactly as designated (for example, the expression "substantially perpendicular" should be interpreted as "at least approximately perpendicular" since it may be possible to select an orientation which is not exactly perpendicular in order to be able nevertheless to substantially fulfill the same function). Further, the terms such as the term of "substantially" used in the present application may also be interpreted as defining that the technical characteristics may be "in general" ("generally"), and often "preferably", as indicated, but that other embodiments or configurations may be within the scope of the present invention.

Figure 1B:
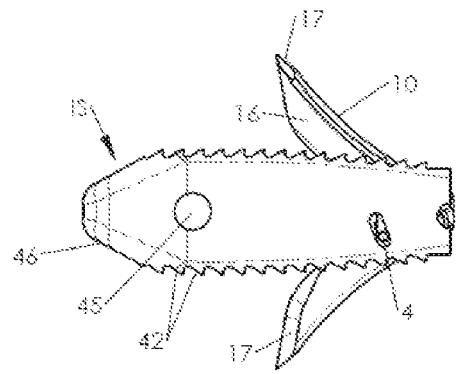

In certain embodiments, said body (10) of the anchoring device (1) includes at least one rib (16) or second body cooperating with at least one groove made in the passage (40) of the implant. Said rib (16) is preferably intended at least for limiting (or even preventing) transverse displacement of the anchor (1) (and therefore also of the implant) with respect to the vertebrae. The rib may also be configured and deployed for stiffening the anchor (1). For example, FIGS. 1D and 2D show anchoring devices (1) provided with at least one rib (16). FIG. 1E shows an implant for which the passage (40) has two grooves for letting through such grooves of the anchoring device. Such a rib may in fact be on various portions of the anchor (1) and have various dimensions for providing good stability of the anchor (1) in the vertebrae. Thus, this rib may in fact form a second body (16) running along the first body (10) of the anchoring device (1). Thus, in certain embodiments, the anchor (1) includes at least two bodies (10, 16) for which the longitudinal axes are parallel with each other, but for which the transverse axes are not parallel with each other. For example, FIGS. 1B, 1D and 2E show anchors (1) including two bodies (10, 16) perpendicular to each other. Preferably, the transverse axes of both bodies (10, 16) are perpendicular to each other giving an L-shaped section to the anchoring device (1), but they may also have an angle different from 90°, for example by giving the device a V-shaped section. Also, it is conceivable that this is in fact a single and same body but which is curved in this transverse dimension, so that the device has a C-shaped section (and it is clear that it is possible to provide other section shapes, H-shaped, U-shaped, etc). This type of layout may be useful since the rigid bodies used in the present invention are more stable than other less solid attachment means such as nails or staples, but, especially the fact of having an anchor for which the width (the dimension transverse to its longitudinal axis) has two edges of different orientations (by the fact that it includes two bodies not parallel to each other or a curved body or a rib), gives the possibility of opposing the movements of the anchor in the bone along at least two different directions. Thus, the anchor is clearly stabilized in the bone and does not risk cutting or cutting out vertebrae by its lateral movements. This possibility of providing a second surface opposing the movements along a second direction is therefore designated here by the term of "two bodies" and of "L-shaped section", whether in fact this is a single curved body or else two bodies (of non-parallel but variable orientations, for example as an L or as a V). Thus, certain embodiments of the invention relate to an anchoring device (1), the body of which included a second body (16) elongated along said longitudinal axis of the first body (10) and extending between the anterior end and the posterior end, the second body (16) being secured to the first body (10) and not parallel to the first body (10), giving the device an L-shaped, V-shaped or C-shaped section mating the internal section of the passage in the implant (IS). This type of advantageous layout may be contemplated regardless of the type of abutments used, i.e. either comprising or not an abutment (13) described in the present application in cooperation with a locking device (or means) 4.

Figure 2A:
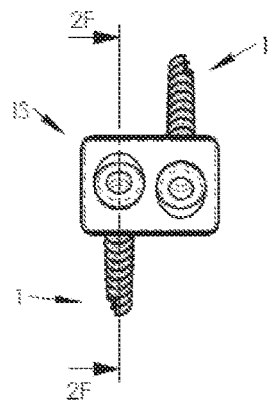
FIGS. 2A, 2B, 2C and 2F represent respectively rear, profile, perspective and sectional views along the plane 2F-2F of the FIG. 2A, of an intersomatic implant provided with an anchoring device of the screw type according to an embodiment.
Figure 2B:
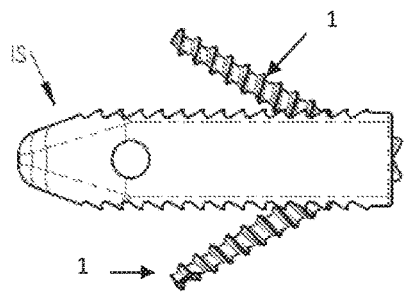
Figure 2C:
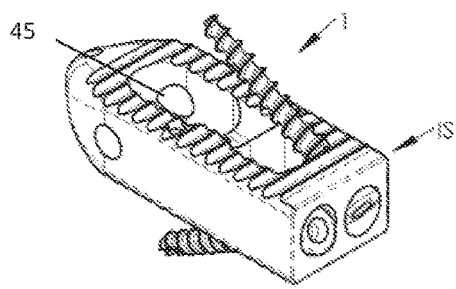
Figure 2D:
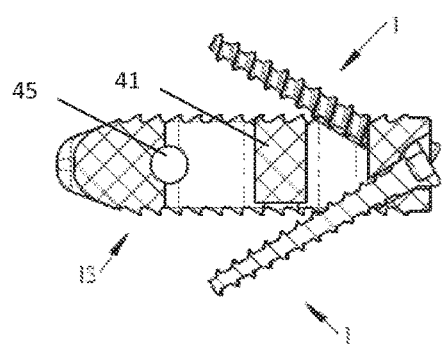
Figure 2E:
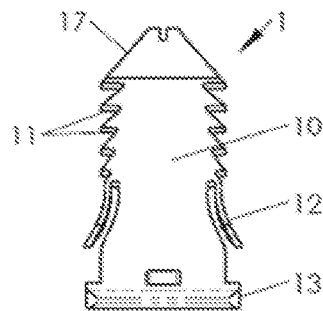
Figure 2F:
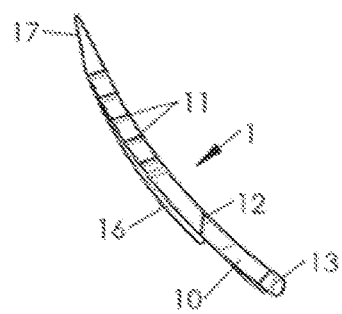

In another way, the anchoring device (1) according to various embodiments of the invention includes at least one retention abutment (13) (sometimes limited to a simple surface) laid out for locking the anchor (1) with respect to the implant (or vice versa). The body (10) is configured, in certain embodiments, so that the anterior end penetrates into at least one vertebra when its posterior end remains in the passage (40) of the implant (IS) or against an edge of the implant (IS), by thereby pressing said implant (IS) against said vertebra by means of at least a retention abutment (13), oriented non-parallel to (or forming an angle with) the longitudinal axis (L) of the body (10) and pressing against a mating surface of the implant (IS) (e.g., on an edge or in the passage (40) of the implant). Preferably on the posterior end of the body (10) of the anchoring device (1) is at least included a withdrawal abutment (13) configured for retaining or locking the anchor (1) in the implant (IS) by pressing the intersomatic implant (IS) against the vertebrae (VI, VS) as illustrated in FIGS. 1A, 2E and 2F. Such retention or such locking of the anchor (1) in the implant may be obtained in various embodiments with different types of latch, lock, abutment, etc. In certain advantageous embodiments, this retention or this locking is obtained by at least one withdrawal abutment (13) which may be oriented according to an angle with respect to (i.e., not parallel to) the longitudinal axis (L) of the body (10) and configured for cooperating with a mating surface of the implant and retaining the device (1) in the implant.

In certain embodiments of the invention, the body (10) of the anchoring device (1) includes at least one flexible withdrawal abutment (12) oriented so as to form an abutment opposing the removal of the anchoring device (1). As particularly visible in FIGS. 2E and 2F, this flexible abutment (12) may be present on both lateral sides of the body (10).

Figure 1C:
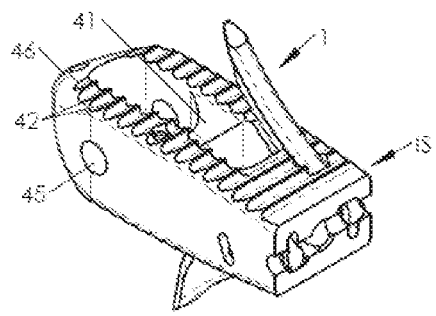
Figure 1D:
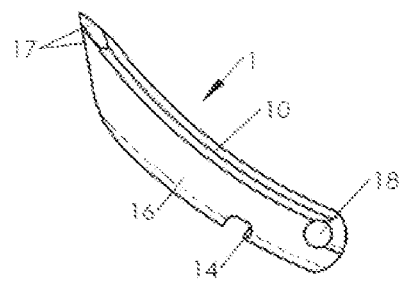
FIG. 1D represents a profile view of the same anchoring device and FIG. 1E represents a top view of the same intersomatic implant.
Figure 1E:
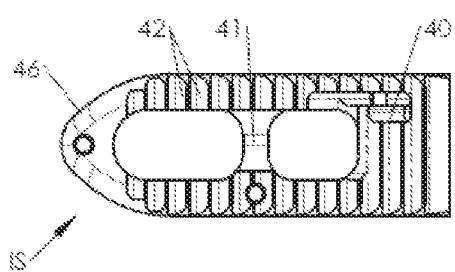
Figure 1F:
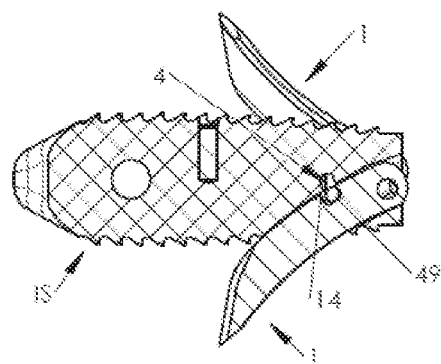

According to an embodiment illustrated in FIGS. 1C and 1D, the intersomatic implant includes a reinforcement (41) crossing right through its cavity and which may be laid out for reinforcing the peripheral wall of the implant. This reinforcement (41) may have different shapes and orientations and may for example be oriented along the axis for inserting the implant (IS) between the vertebrae. In various embodiments, the reinforcement (41) may have a less significant height than the remainder of the implant (IS). This less significant height of the reinforcement (41) with respect to the remainder of the implant gives the possibility to the implant of fitting possible shape irregularities of the vertebral plates.

According to a particularity of the invention, the intersomatic implant (IS) may have different shapes as long as they have a passage (40), includes at least one hooking-up means (44) intended to cooperate with a gripping end of an implantation instrumentation. These hooking-up means (44) may, according to the embodiments be associated with a particular shape of the implant (IS) or of the body (10) in proximity to the hooking-up means (44) in order to allow good cooperation with the instrumentation or even include one of these particular shapes cooperating with mating shapes of the instrumentation. Also, as mentioned earlier, the intersomatic implant (IS) may include a cavity in its center or not, in so far that it is frequent to implant several intersomatic implants in a same intervertebral space (in as much that the dimensions allow this). The thereby implanted cages are generally used for closing the bone tissue (graft) which will grow inside the intervertebral space and allow fusion (arthrodesis) of both vertebrae between which it is implanted. The purpose of the implant (IS) is to restore or maintain a space between the vertebrae.

In an embodiment of the invention, the anchoring device (1) includes at least one abutment (14) (sometimes limited to a simple surface) mating an abutment not visible in the figures (or a surface also) of a means (or device) for locking (4) laid out for locking the anchor (1) with respect to the implant (or vice versa). This locking means (4) is located on or in the actual intersomatic implant, i.e. the locking means (4) is housed in a housing inside the intersomatic implant (IS). This locking means (4) preferably comprises a body retained in the implant and provided with at least one flexible portion and with at least one abutment (49), cooperating with said abutment (14) of the device (1), generally by the contact of their mating abutment surfaces (49) for locking the device (1) with respect to the implant (IS). In various embodiments, one benefits from this flexibility which allows that the locking means facilitates the passing of the anchor before its abutment engages with the mating abutment of the anchor. For example, the insertion of the anchoring device (1) in the passage (in which the locking means juts out at least slightly) gives the possibility of pushing back said abutment (49) of the locking means (4) and also allows mutual engagement of both abutments (14, 49), of the anchor and of the locking means (4), when they are found facing each other, by the elastic return of the flexible portion. In another example, as detailed further on, it is possible to push the locking means by means other than the body of the actual anchor, such as for example with a tool, and when the action exerted on the locking means is released, the latter locks the anchor brought into a final position in the implant.

Thus, the posterior end of said body (10) of the anchoring device (1) includes at least one abutment (14) oriented non-parallel to the longitudinal axis of said body (10) and mating at least one abutment (49) of at least one locking means (4) of the device (1) relatively to the intersomatic implant (IS), said locking means (4) which equips the implant (IS) being provided with at least one flexible portion allowing said abutment of the locking means (4) to be pushed back on the one hand for inserting the anchoring device (1) into the passage (40), and mutual engagement of both abutments (14, 49) on the other hand when they are found facing each other, by the elastic return of the flexible portion.

Before the growth of the graft and fusion of the vertebrae, the cage (1A, 1B) should remain properly in place in the discal space and various embodiments of the present invention facilitate its immobilization. Before implantation of the anchoring device (1) allowing the implant (IS) to be maintained in position, there sometimes exist a risk that the implant moves in the discal space. In certain embodiments, at least one of the upper and lower surfaces of the wall of the implant (IS) will include notches or teeth (42) avoiding the displacement of the implant between the vertebrae between which it is intended to be implanted. Thus, at least one of the upper and lower surfaces of the peripheral wall includes notches (42) avoiding the displacement of the intersomatic implant (IS) between the vertebrae between which it is intended to be implanted. According to different embodiments, these notches (42) or other stabilization means may have different orientations, so as to avoid displacement of the implant (IS) in one or several directions. For example, the notches (42) may be substantially parallel with each other and all oriented perpendicularly to the insertion axis of the implant (IS), but the notches (42) may on the contrary have different orientations on different portions of the implant (IS), so as to avoid displacement in any direction. It will be noted that on the various figures of the present application, the exemplary cages illustrated include notches over the totality or quasi-totality of their vertebral contact surfaces, but not on the peripheral wall of the cage. The posterior portion of the vertebral contact surfaces of the cage does not include any notch in these examples. However, it is possible in various embodiments to make notches on this portion or on other peripheral portions, provided that these notches do not interfere with the various abutments, ribs, and/or other elements and characteristics which may be configured on these implants and/or on the anchors which may be associated with them.

In certain situations, notably depending on the vertebrae between which the implant (IS) has to be implanted, it is desirable that the implant imposes, fits or corrects a lordosis, a kyphosis or even scoliosis, in addition to maintaining the space between the vertebrae. Thus, depending on the vertebrae between which the intersomatic implant (IS) has to be implanted, it is desirable that the implant gives the possibility of imposing lordosis or kyphosis in addition to maintaining the space between the vertebrae. Certain embodiments, the mean planes passing through the upper and lower surfaces of the implant (IS) form an angle (A1) oriented along an anteroposterior axis of the intersomatic implant (IS), giving the possibility of imposing lordosis or kyphosis to the vertebrae between which the intersomatic implant (IS) is intended to be implanted. According to an embodiment of the invention, the mean planes passing through the upper and lower surfaces of the intersomatic implant (IS) are substantially parallel with each other.

In certain embodiments, the peripheral wall includes two passages (40) each oriented towards one of the upper and lower surfaces so as to allow anchoring of the anchoring device (1) in each of the vertebrae between which the intersomatic implant (IS) is intended to be implanted. In other embodiments, the peripheral wall includes at least two passages (40), located side by side, each of them defining a possible insertion axis for the anchoring device (1) in the intersomatic implant (IS) and indirectly, a possible insertion axis of the intersomatic implant (IS) between the vertebrae.

Further, in certain embodiments, the peripheral wall includes at least one chamfer (46) on at least one peripheral portion of at least one of its upper and lower surfaces so as to facilitate insertion of the intersomatic implant (IS) between the vertebrae. As particularly visible in FIGS. 1B and 2B, this chamfer (46) of the implant may be substantially located in the implantation axis of the implant. This chamfer (46) or bevelled profile gives the possibility of facilitating the implantation of the intersomatic implant by giving it a substantially smaller height on its leading edge (the one intended to be inserted first) than on the remainder of the implant. The body of the intersomatic implant (IS) includes, at an anterior portion (according to the convention of directions described elsewhere in the present application, therefore opposite to the posterior portion including the passage (40) for the anchor (1)), at least one bevelled portion (46), such as for example at least one chamfer (46) on at least one peripheral portion of at least one of its upper and lower surfaces, so as to facilitate the insertion of the implant (IS) between the vertebrae (VI, VS). It will be noted that the bevelled portion (46) on at least one of the upper and lower surfaces should not be too large relatively to the dimensions of the body (for example a length of less than ⅓ of the length of the implant) in order to leave a sufficient contact surface of the upper and lower surfaces with the vertebral plates. One has in another embodiment of the present invention, in which only a portion of the junction between at least one of the upper and lower surfaces on the one hand and the anterior portion of the cage which is beveled on the other hand (for example the anterior third portion in the case of an intersomatic cage).

Figure 5A:
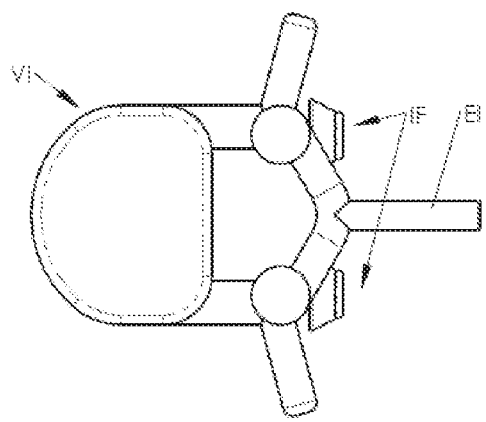
FIGS. 5A, 5B, 5C and 5D represent respectively underside, front profile perspective and rear perspective views of an arthrodesis system according to an embodiment comprising an intersomatic implant and two facet implants for arthrodesis of two adjacent vertebrae, at least one of which is visible in each of these figures.
Figure 5B:
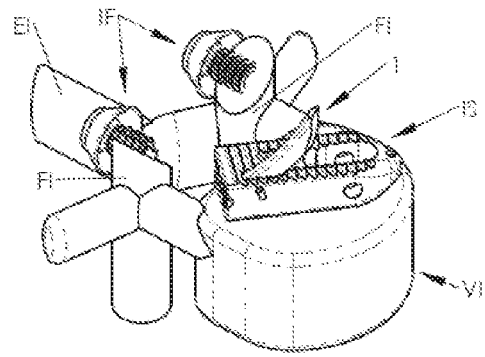
Figure 5C:
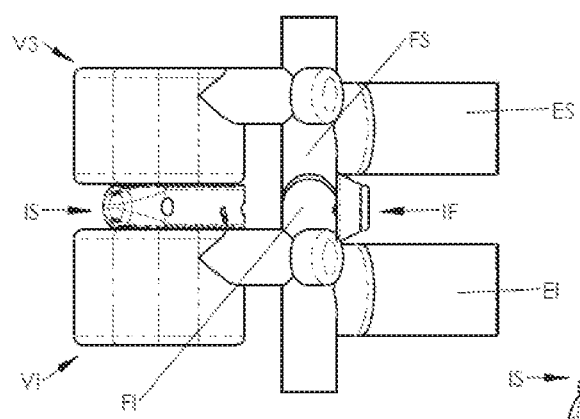
Figure 5D:
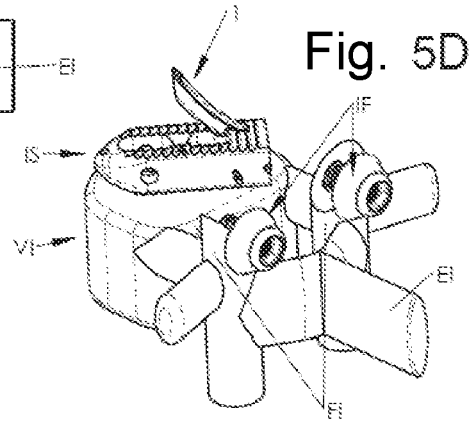
Figure 6A:
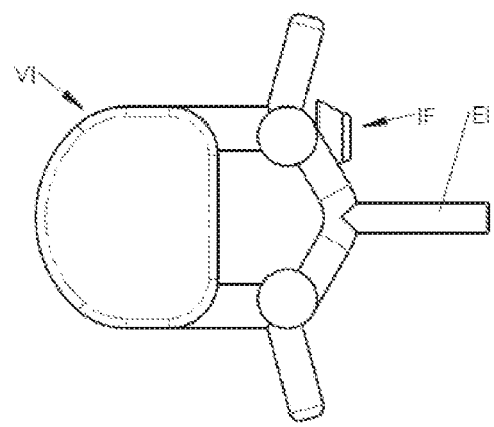
FIGS. 6A, 6B, 6C and 6D represent respectively underside, front perspective, profile and rear perspective views of an arthrodesis system according to an embodiment comprising an intersomatic implant and a facet implant for the arthrodesis of two adjacent vertebrae, at least one of which is visible in each of these figures.
Figure 6B:
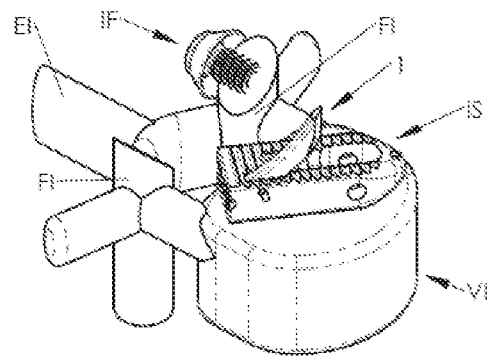
Figure 6C:
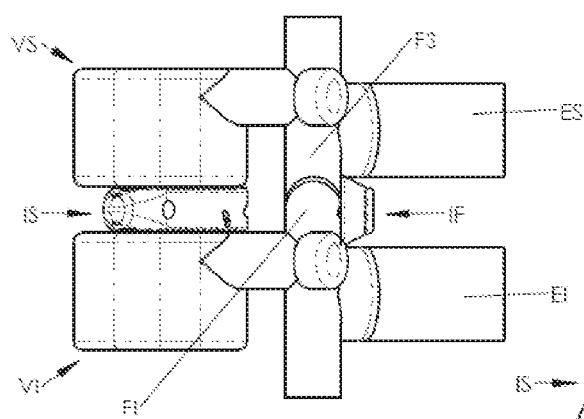
Figure 6D:
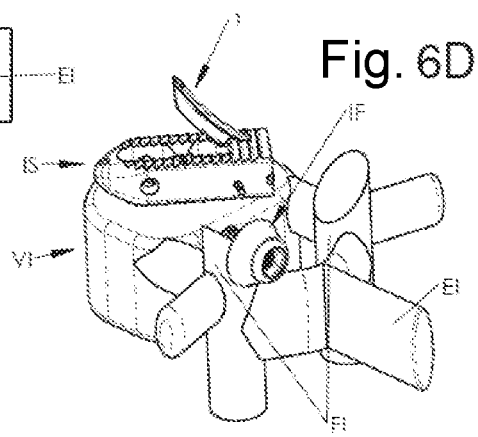
Figure 7A:
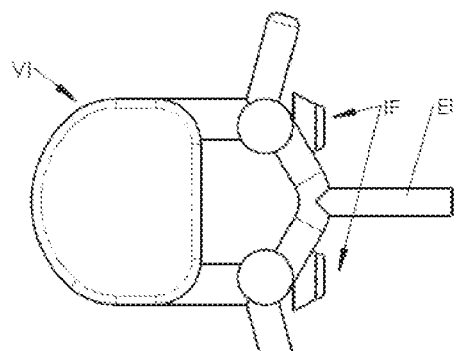
FIGS. 7A, 7B, 7C and 7D represent respectively underside, front perspective, profile and rear perspective views of an arthrodesis system according to an embodiment comprising two intersomatic implants and two facet implants for the arthrodesis of two adjacent vertebrae, at least one of which is visible in each of these figures.
Figure 7B:
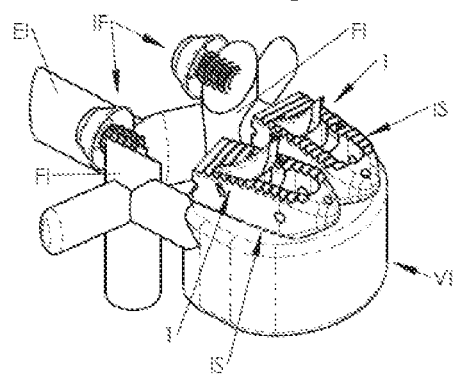
Figure 7C:
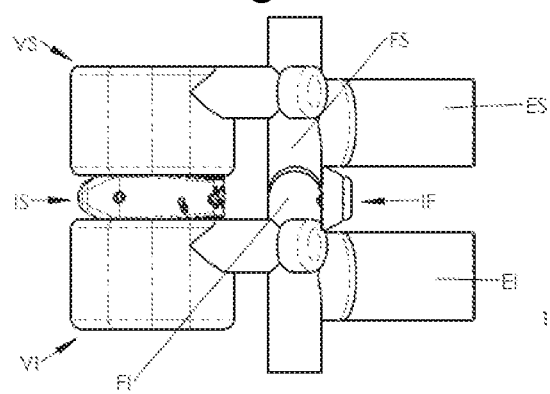
Figure 7D:
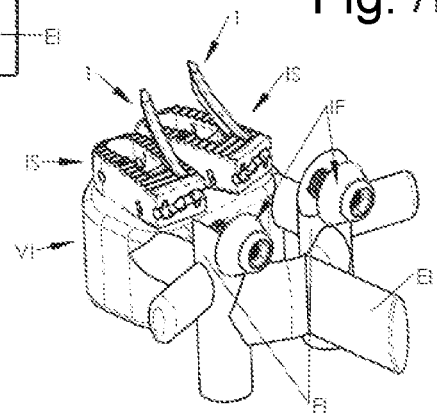

As particularly visible in the example of the intersomatic cage (IS) of FIGS. 5B and 5D, the anterior end of the cage substantially has the shape of a bevel or a chamfer or a shell tip (46), for optimizing the penetration of the cage between the vertebrae (VI, VS), notably when the separation of said vertebrae is insufficient. The chamfer or bevel (46) may in fact be present on both lower and upper surfaces of the implant (IS). This chamfer (46) or bevelled profile gives the possibility of facilitating the implantation of the implant (IS) by giving it a substantially smaller height on its leading edge (the one intended to be inserted first) than on the remainder of the cage. Further, it is also possible to bevel the side faces at the anterior end of the implant so that it has the shape of a shell facilitating its penetration between the vertebrae.

On the other hand, it is possible to bevel at least one portion of the junctions of at least some of the side faces with the upper and lower surfaces. In particular, the intention is sometimes to insert the implant in an orientation having pivoted by 90° around its longitudinal axis with respect to the final position (the one in which the upper and lower surfaces are in contact with the adjacent vertebrae). Indeed, as explained earlier, the dimensions of the cage intended for implantation via a posterior or transforaminal route may be such that the dimensions of the height of the cage are greater than that of the width of the cage. It may therefore be desirable to first insert the cage with its side faces positioned upwards and downwards towards the rachis (the upper and lower faces being found positioned laterally with respect to the rachis), and then pivot the cage so as to restore the height of the intervertebral space to the desired value (obtained by means of the fact that the height of the cage has the selected value). The implant is therefore inserted in an orientation having pivoted by 90° around its longitudinal axis with respect to the final position, and then it is pivoted in order to be placed in its final position once it is in the discal space. In this type of implantation, it may be desirable that at least portion of at least one portion of the junctions between the side faces and the upper and lower surfaces be bevelled so as to facilitate rotation of the implant between the vertebrae. Such bevels or rounded shapes or any shape for the cage may be provided even if this is not the type of implantation which is intended, but a cage is generally preferred which provides the maximum contact surface for a given size and junctions which are not too much rounded are therefore preferred. It is then preferable to provide such bevels when this rotation is intended during the implantation upon inserting the implant (IS) in a position having pivoted by 90° around its longitudinal axis with respect to the final position in which the upper and lower surfaces are in contact with the adjacent vertebrae between which the implant (IS) is intended to be implanted. Generally, it is sufficient that only a portion of the junctions is bevelled, such as for example a single junction on both junctions between the side faces and the upper surface and a single junction on the two junctions between the side faces and the lower surface. Junctions which are opposite (the left face/lower surface junction opposite to the right face/upper face junction, for example), as for example visible in FIG. 1B, are then preferably selected. Further, generally and notably it is sufficient when the upper and lower surfaces are tilted relatively to each other (e.g., when the implant is less thick at its posterior end than at its anterior end), that only one portion of these junctions is bevelled. Indeed, it is sufficient to bevel the portion at which the cage is thicker, as for example visible in FIG. 1B.

On the other hand, in certain embodiments, the body of the anchor (1) is provided with notches or teeth (11) oriented so as to be opposed to the removal of the anchor (1) once it is implanted in a vertebra, as visible in FIGS. 2E and 2F.

It will be noted generally that the passages, the holes, the notches, the teeth, the abutments, the housings, the tabs and other elements of the various objects of the invention (anchors, implants, instruments . . . ) may be formed by various methods such as by machining, piercing, molding, welding, etc and that the examples given here should not be interpreted in a limiting way.

Implants of the Facet Type (IF):

Various embodiments of the facet implant (IF) according to the present invention may be used for arthrodesis of at least two adjacent vertebrae (VI, VS), as illustrated in a non-limiting way in FIGS. 4A to 4E and 12A to 12D.

It will be noted that provision may be made for an interfacet implant and/or a transfacet implant. Indeed, the present invention notably details implants, so-called "facet" implants, intended to be implanted between the articular facets of the vertebrae (so-called "inter-facet" implants) and/or implanted through these articular facets of the vertebrae (so-called "transfacet" implants). Various embodiments of the present application are also adapted to an implantation in vertebral pedicles (so-called "pedicular" implants) or at the sacrum-iliac joint or in various types of bone structures either spinal or not, although the characteristics of the implants described in the present application make them particularly useful for their use in the rachis.

From the prior art such as from patent FR 2 726 171 B1, implants are known with the shape of a hollow cylinder provided with a thread for the bone screwing, forming a screw in which a conduit and grooves are made for providing a grafting space allowing the insertion of bone or cement tissue or substitute for facilitating the fusion of the structures in which the screw is implanted. It will be noted that vertebral articular apophysis (or articular processes or pedicular facets) are designated here by the term of "articular facet", since each vertebra is jointed with the one above and below by articular facets which are posterior and the invention is useful for treating these articular facets, but it is possible to possibly use various embodiments on other structures, notably vertebral structures, such as for example costal or sacrum-iliac facets if need be. Articular apophyses protrude above and below the base of the transverse apophyses of the vertebrae, rearwards from the pedicles. At the lumbar level for example, the upper articular apophyses are separated from each other by a larger distance than the one which separates the two lower ones. The articular facets which they support have the shape of a vertical gutter, the concavity is turned to face rearwards and inwards, a gutter in which will be placed the lower articular apophyses which have an articular surface which is convex in the reverse direction, i.e. towards the front and towards the outside. The lower articular apophyses provide a convex articular surface, in the form of a cylinder segment, which faces outwards and slightly forwards. This surface slides in the concavity of the upper articular apophysis of the vertebra located below. These structures are therefore important for the stability of the vertebrae one upon the other and it will moreover be noted that bone deficit (or "lysis") of the isthms (or "pars interarticularis") located at their base is often responsible of spondylolisthesis (sliding of a vertebra with respect to the other adjacent ones) which generally lead to degeneration of the intervertebral discs. When it is sought to produce vertebral arthrodesis, it is therefore sometimes desirable to use a facet implant for attaching the lower articular apophyses of a vertebra to the upper articular apophyses of the adjacent vertebra. These facet implants may either be "inter-facet", i.e. they are inserted between the articular surfaces, or "transfacet", i.e. they are inserted through the articular apophyses for attaching the articular surfaces together. The interfacet implants are generally set into place in the articular joint, by identifying the approach axis and for example by positioning a pin used as a guide for the implant, which is often splined (i.e. hollow). A problem in the field relates to the solidity since it is desirable to guarantee the integrity of the implant in spite of its small size and of its often hollow arrangement. Generally, in the case of an implantation at the articular facets, the use of implants is preferred so as to secure the (left and right) facets which joint together two adjacent vertebrae, but this use is of course not limiting.

Generally, the facet implant (IF) includes, on the one hand a body (80) elongated between a free end and a head (78), along a longitudinal axis and turns (72) of at least one threading on the other hand on at least one portion of said body (80) in proximity to the free end, along the longitudinal axis. Further, the body (80) of the facet implant (1) preferably includes at least one longitudinal internal conduit (71) on at least one portion of the body (80) along the longitudinal axis and/or windows (75) crossing the walls of the body from the outside of the body as far as the longitudinal internal conduit (71) in a so-called transverse plane not parallel to the longitudinal axis. Said body (80) may have the shape of a screw or of a wedge.

In certain embodiments, this longitudinal internal conduit (71) is obtained by at least one first central machining parallel to the longitudinal axis and at least one second machining operation in a so-called transverse plane, not parallel to the longitudinal axis and crossing the walls of the body (80) as far as the longitudinal internal conduit (71) by making windows (75) communicating between said longitudinal internal conduit (71) and the outside of the body (80). Thus, the implant includes an internal conduit (71) which at least preserves one portion of said turns (72) and the wall of the body (80) behind the turns, and preserves non-machined portions thereof on the periphery of said body (80).

In some of these embodiments, the second machining operation may for example be carried out tangentially to the periphery of the body (80) resulting in windows (75) which flare from the inside towards the outside of the body (80), as for example illustrated in FIGS. 4A, 4B, 11A and 11B. However, alternatively, the second machining operation may be carried out substantially radially (or along an oblique axis between the radial orientation and the tangential orientation) so as to obtain windows having at least one sharpened outer lateral edge.

In certain embodiments, said free end of the body (80) is self-drilling. By the term of "self-drilling", is meant here the fact that this end is capable of itself drilling bone tissue. Such a functional definition may find application simply by a sharpened shape of the end but may also be advantageously obtained by a split head or by the fact that a window (75) is present on an extreme distal portion and provides a cutting surface giving the possibility of drilling into bone tissue. In another embodiment, it is possible to provide a notch on a cylindrical or conical or frustoconical end in order to allow the free end of the body (80) to be self-drilling. But it is also possible to provide that the drilling function be obtained by at least one window (75) at the distal end. Thus, for example, a window (75) may be made which extends over several turns (72) and which provides a cutting edge giving the possibility of more easily sharpening the bone.

Figure 4A:
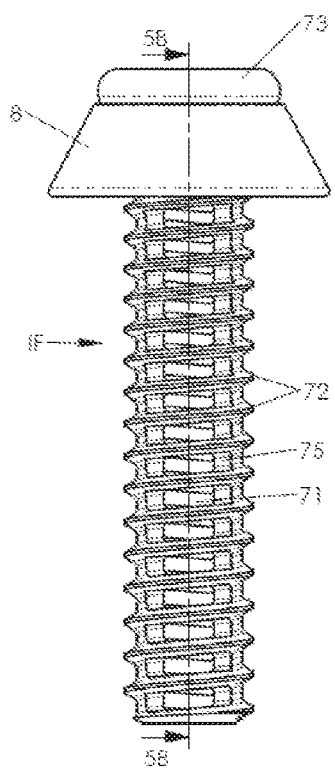
FIG. 4A represent a profile view of a facet implant according to an embodiment.

Thus, in certain embodiments, said windows (75) are shifted relatively to each other along (or rather around) the longitudinal axis (not shown in the figures), while in other embodiments, said windows (75) are aligned with each other along the longitudinal axis, for example illustrated in FIGS. 4A and 11A. It will be noted that it is also possible to provide a combination of these layouts, by providing windows aligned on a portion and windows shifted on another portion. When they are shifted relatively to each other, it is generally preferred that a more proximal window is shifted relatively to a more distal window on the side which corresponds to the screwing direction. Thus, for example, with a threading oriented in the clockwise direction, a proximal window will be shifted left with respect to a more distal window, so as to improve the sharpening of the bone or cartilage which may be gradually obtained by the successive windows during the screwing.

In certain non-exclusive embodiments, but however independent from those with two non-parallel machinings defined above, said windows (75) of the interfacet implant (IF) advantageously have at least one sharpened outer edge. Indeed, regardless of how the conduit and the windows are obtained, it may be useful to provide at least one sharpened outer edge for the windows (75). In particular, it is generally preferred that the sharpened edge be the one which checks first the bone during the screwing of the implant, so that this sharpened edge may gradually be into the bone (for example by cutting shavings) during the screwing. Thus, when the windows (75) are obtained with a second machining operation, the latter may for example be made along a radial or oblique axis as explained above, so as to obtain at least one sharpened leading edge, such as for example illustrated in FIGS. 4D and 4E.

Thus, in certain embodiments, said head (78) of the implant (80) closes the longitudinal internal conduit (71) or includes means for closing the longitudinal internal conduit (71). Such closing means give the possibility of providing an implant able to be slipped onto a pin assisting the implantation like in the prior art and nevertheless gives the possibility of blocking up the implant after implantation.

As regards the pitch of the thread, i.e. the spacing of the turns along the longitudinal axis, the present application also provides various types of non-limiting layouts which may be useful depending on the conditions. In particular, in certain embodiments, the turns (72) of the thread (or by extension the threading (72) of the implant) has a variable pitch which shortens towards the head (78). Also, in certain embodiments, the body (80) is provided with several threadings (72) of different pitches, the pitch of a thread located on the side of the free end being of a larger size than the adjacent thread located on the side of the head (78). Preferably, the pitch of a thread located on the side of the free end is of a larger size than the adjacent thread located on the side of the head (78), so that the pitch of the threading is gradually reduced when advancing towards the head. This type of arrangements with a variable pitch gives the possibility of obtaining a compressive effect. Indeed, when such an implant with variable pitch or comprising several threads with decreasing pitches is screwed on, a compression effect is obtained, which is for example particularly useful in the case of a screwing in a bone structure where it is sought to well flatten the structures against each other, such as for example a transfacet implantation.

Figure 12A:
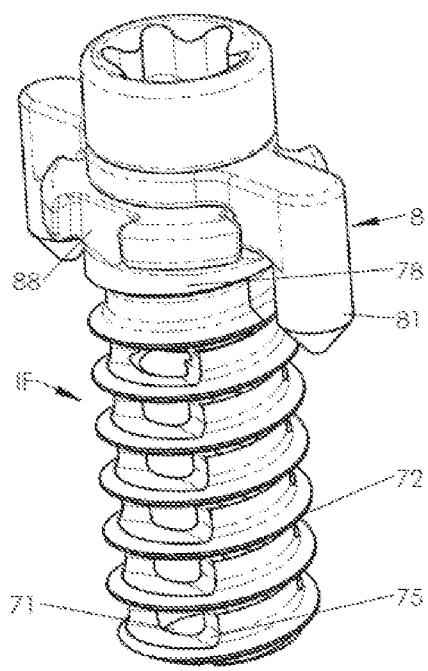
FIGS. 12A, 12B and 12C respectively represent perspective, front and profile views of a facet implant according to another embodiment.
Figure 12B:
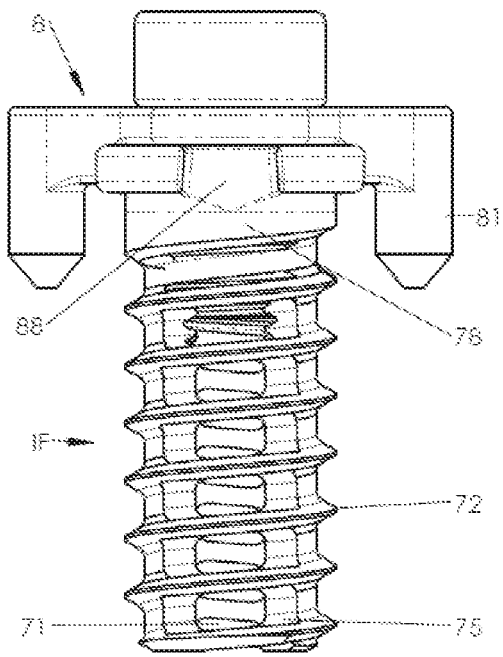
Figure 12C:
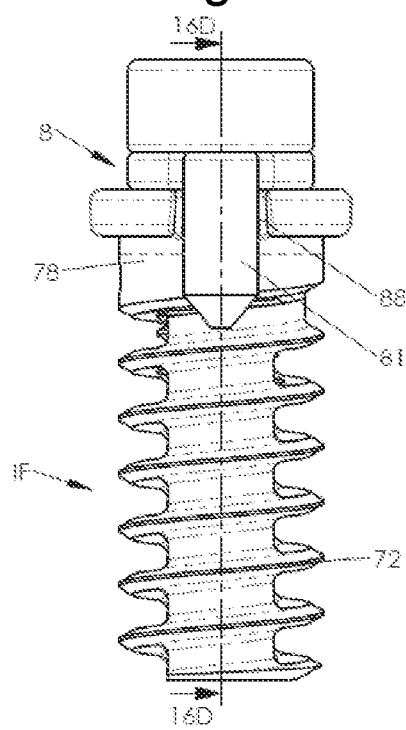
Figure 12D:
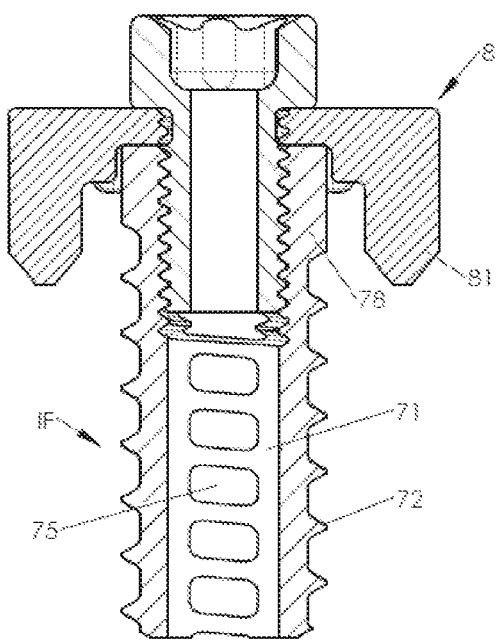
FIG. 12D represents a sectional view along 16D-16D of FIG. 14C of the same implant.
Figure 13A:
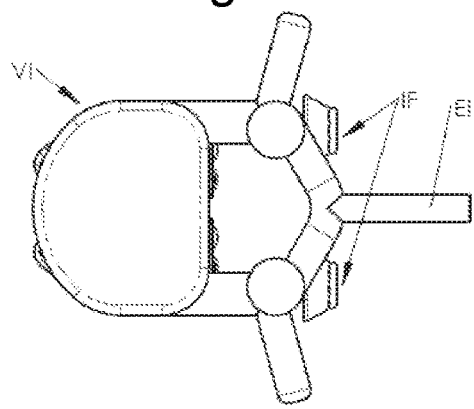
FIGS. 13A, 13B, 13C and 13D respectively represent underside, front perspective, profile and rear perspective views of an arthrodesis system according to an embodiment comprising an intersomatic implant and two facet implants, for the arthrodesis of two adjacent vertebrae, at least one of which is visible in each of these figures.
Figure 13B:
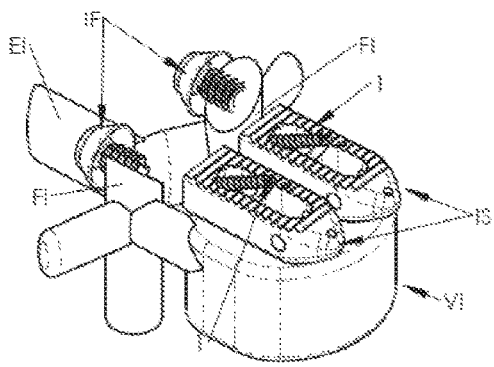
Figure 13C:
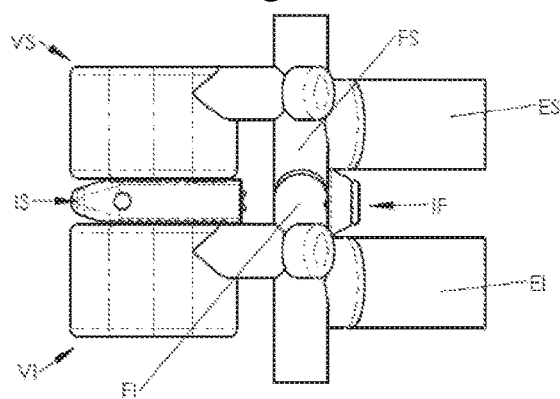
Figure 13D:
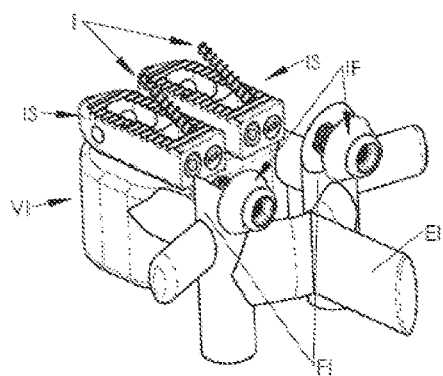

On the other hand, in certain non-exclusive embodiments, but however independent from those with two machining operations and/or with a sharpened edge as defined above, said head (78) of the implant (IF) is provided with stabilization means (e.g., compression, locking, supporting means) of the implant, intended to be supported on the bone tissue around said head (78) (these stabilization means optionally comprising locking means for securing them on the implant). Various embodiments are described hereafter for the stabilization means but one skilled in the art will understand from this functional definition that the implant is provided so that its head (which is generally the portion which subsists outside the bone tissue or the articular space) is stabilized on the bone tissue (on a bone surface or on the edges of the joint). In some of these embodiments, the stabilization means include at least one stabilization element (8) forming a sort of staple comprising at least two rods (81) substantially parallel to the longitudinal axis and able to penetrate the tissue around the head (78) and optionally of a portion of said body (80) in proximity to said head (78). Examples of such stabilization means (8), as illustrated in FIGS. 12A and 12D, comprising a ring intended to be slipped onto a portion of the head and at least one spike intended to be planted into the surrounding tissues. In some of these embodiments, said rods (81) of the stabilization element (8) have a sharpened free end. The term of "sharpened" in the present description in fact designates more broadly the fact that a structure is able to penetrate the bone tissue, by therefore covering bevelled structures as well as spiked structures and in a non-limiting way. Further, in certain embodiments, said rods (81) are connected together by a ring, as described in the prior art WO 2016/016474, making the stabilization element (8) able to be mounted on said head (78), but one skilled in the art will appreciate that this type of mounting on the head is only an illustrative and non-limiting example since various arrangements will give the possibility of providing means for mounting the stabilization means on the head (or any other portion of the implant optionally). According to various alternatives, the ring (83) is slipped or screwed onto a high portion (83) which juts out from the head (78), while in other alternatives, the ring lies on the head and its opening is able to receive a low portion (83) of the locking means (73) which are attached in the head of the implant. It will be noted that the figures showing threadings and trappings for attachment of locking means on the head, but that various other types of layouts are possible, as detailed above with reference to the means for closing the implant.

In certain embodiments, in particular those comprising a stabilization element (8) provided with two rods (81) intended to penetrate the bone tissue around said head (78), the latter includes at least two notches (88) able to receive said rods (81) or shoulders (82) positioned along said rods (81). Such notches (88) give the possibility of imposing the position of the rods (81) around the implant, so that it is possible to provide that they be ideally positioned with respect to the treated bone structures (notably so that they are each planted into one of the adjacent vertebrae during interfacet implantation). Further, the presence of a shoulder (82) (and of material between the centre of the stabilization element and said rods) gives the possibility of maintaining said rods away from the body (80), so that these rods may be planted at a distance ensuring better stabilization than if they had been closer to the body of the implant.

In certain embodiments, the stabilization means include at least one stabilization element (8) with a shape of a bell mounted on (or secured to) the head (78) and the periphery (81) of which is intended to be supported on the bone tissue surrounding the head (78), such as for example illustrated in FIGS. 5A, 5B and 5C. In various embodiments, the bell is mounted so as to be secured to the head is formed in one piece with the head or is attached above. In other embodiments, the bell is movably mounted around the head. Further, the bell may be in the same material as the body of the implant (generally a solid metal material such as for example titanium), but it is possible to provide a bell in another material, notably more flexible so that it is crushed upon final screwing of the locking means and thus ensures efficient compression. A possible and useful material for this type of alternative embodiments is PEEK well known in the field.

In certain embodiments, the bell is mobile and provides a support of the "polyaxial" type i.e. may be locked in diverse positions relatively to the longitudinal axis of the implant. For example, in certain of these embodiments, said head (78) has a peripheral lower surface (780) in the form a sphere portion, such as for example illustrated in FIGS. 4B, 4D and 4E. Such a surface is generally provided so as to mate an internal upper surface of said bell (8) thus jointed on the head (78) of the implant, such as for example illustrated in FIG. 4B, so as to allow adjustment of the orientation of the bell with respect to the axis of the head.

Figure 4B:
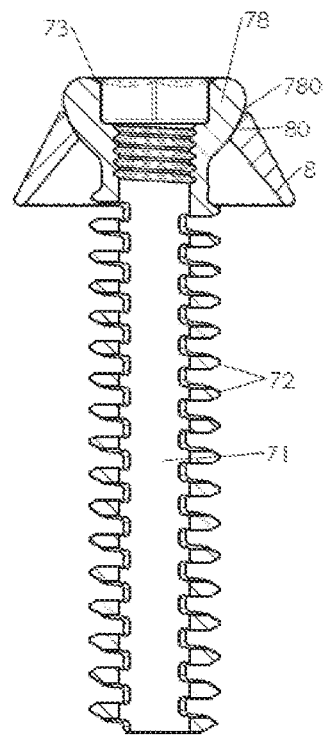
FIG. 4B represents a sectional view along the plane 5B-5B of FIG. 4A and FIGS. 4C, 4D and 4E represent perspective views, of a stabilization element and of two alternatives of a facet implant according to an embodiment, respectively.
Figure 4C:
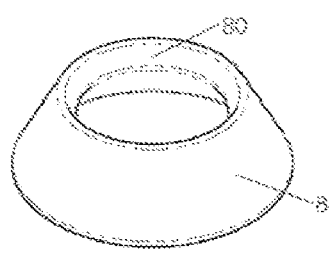
Figure 4D:
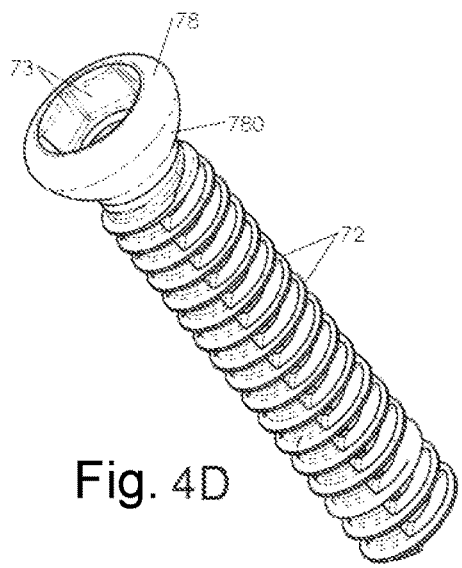
Figure 4E:
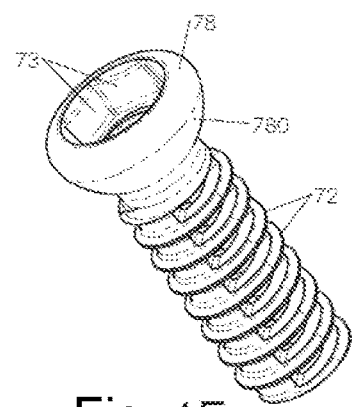

In certain embodiments, said bell (8) includes at least one spike or tooth on its periphery (81) for facilitating bone anchoring, such as for example illustrated in FIGS. 4A and 4B. This type of layout of the low portion of the bell, intended to be supported on the bone tissue, gives the possibility of improving the adhesion of the bell on the latter and thus improves the stability of the implant. In embodiments comprising a longitudinal internal conduit (71) and windows (75) obtained by respectively at least one first machining operation and at least one second machining operation, the second machining operation preserves the material of the body (80) behind the turns (72), such as for example illustrated in FIGS. 4A, 4B, 11A and 11B. Thus, one skilled in the art understands that the implant which results from this is improved by the fact that it has turns which penetrate more deeply into the tissue, as if they were larger, since the material around the turns has been removed by the machining operation 15 (thus reducing the residual width of the body) and that the pressure present in the surrounding environments, in particular in the case of an implantation at an articular level, will cause the turn to sink in more deeply into the bone. Further, the solidity of the implant is improved by the material preserved by the machining operation, whereas in the prior art, only the thread 20 is preserved and the turns (12) are the only ones for supporting the significant forces during and after screwing. Thus a stable and solid implant is obtained.

In these embodiments, said stabilization means preferably include locking means (73) supported on the stabilization element (8) for maintaining it pressed against the bone tissue.

Moreover, it will be noted that in many embodiments illustrated in the figures, the windows (75) are made between the turns (72) of the threading and generally between the totality (or the quasi-totality) of the turns. However, it is possible to make these windows only on a portion of the turns. Thus, at least one portion of said windows (75) are for example separated by at least two turns (72) without any windows (75). Conversely (but not exclusively and in a way which may be combined with the detailed embodiments above), like for the free end, it is possible to provide on diverse portions (proximal, median or distal portions) windows which extend over several turns rather than being confined to the space between two turns. Thus, in certain embodiments, at least one portion of said windows (75) are made on several turns (72).

The terms of "head" and of "free end" are used in the present description with reference to the fact that the implant generally appears in the form of a screw, with a generally cylindrical or conical or frustoconical body (80) but these turns and these forms of the implant should not be considered as limiting. Indeed, the periphery of the threading is substantially cylindrical in spite of the conical or frustoconical shape of the body of the facet implant (IF). On the other hand, the diverse portions of the implant are designated in the present application by the terms of "proximal" meaning "in proximity to the head", or "distal" meaning "in proximity to the free end" or further "median" meaning "substantially in the middle of both ends", but it is clear that these turns are not either limiting and that one skilled in the art will appreciate that the position of these portions may vary along the longitudinal axis. Further, the term of "significantly" or "substantially" is used with reference to various characteristics for indicating that they may be exactly as defined or be approximately as defined. For example, the expression "a substantially planar shape" should be understood as referring to an approximately planar shape since one skilled in the art may vary the exact shape in so far that it would retain a globally planar shape fitting the relevant technical requirements. Also, the present invention may define characteristics without this approximation specification by the terms of "significantly" or "substantially", but it will be clear to one skilled in the art that this notion applies even in the absence of such turns. Further, the term of "machining" is used here in a non-limiting way for referring to the manufacturing of the implant and it is clear that this term in fact covers any type of manufacturing techniques, such as for example, borings, piercings or millings, but also spark erosion or any type of technique giving the possibility of making surfaces or housings on or in the implant. Also, the term of "transverse" is used in order to indicate that the second machining operation is in a plane not parallel with the longitudinal axis and tends to indicate that it is perpendicular to the longitudinal axis, but one skilled in the art will understand, notably because of the oblique orientation of the turns of a threading, that this plane (which is therefore substantially transverse) is not necessarily perpendicular to the longitudinal axis and will generally be oriented rather obliquely, preferably parallel to the turns.

Implants of the Interspinous Type (IE):

Diverse embodiments of the interspinous implant (IE) according to the present invention may be used for arthrodesis of at least two adjacent vertebrae (VI, VS) as illustrated in a non-limiting way in FIGS. 3A to 3E.

Interspinous implants should give the possibility of giving back height between the spinous processes and maintaining this height (relieving the articular facets, the nerve roots, the disc, etc.) notably upon awaiting arthrodesis (bone fusion). They should be stable between the spinous processes, notably at the lumbar level, by having a means for either adhering or not on the spinous processes. Further, it is generally desirable to have different heights and/or widths and/or depths of the implants, notably for adapting them at best to their implantation site. Moreover, in certain cases immobilization of both spines is preferred, while in other cases, mobility is preferably retained. Sometimes it is also desired to control the extent of the mobility, notably the flexure and rotation movements of the vertebrae.

The present invention relates to an interspinous implant (IE) intended to be implanted between the spinous apophyses of two adjacent vertebrae. In the present application, spinous apophyses or spinous processes of the vertebrae are designated by the term of "vertebral spine", "dorsal spine", "spinous process" or quite simply "spine". The spines are the most posterior structures of the rachis and therefore potentially the most rapid to access (it is moreover possible to feel them under the skin from C7 to L5), which makes certain interspinous implants easy to implant but may impose stability and implantation constraints as discussed in the present application. Thus, in the present application one refers to the space which separates two adjacent spines by the term of inter-spinous space. Certain embodiments allow insertion of several implants between the successive interspinous spaces of several (more than two) adjacent vertebrae, as detailed in the present application.

The dorsal spines (EI, ES), generally substantially aligned in the median sagittal plane (or approximately oriented in this plane) substantially have a shape of a stud or plate, with a coronal section generally oblong or elliptical, with an end (a crest) pointing towards the rear of the patient. The spines have, with reference to the longitudinal axis of the rachis, an upper edge (E2), a lower edge (E3) and two opposite side faces (E4, E5).

Figure 8A:
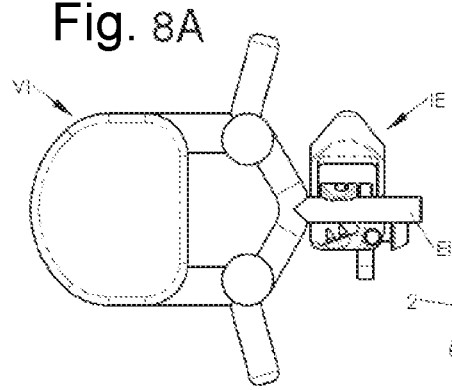
FIGS. 8A, 8B, 8C and 8D respectively represent underside, front perspective, profile, rear perspective and top views of an arthrodesis system according to one embodiment, comprising two intersomatic implants and an interspinous implant, for the arthrodesis of two adjacent vertebrae, at least one of which is visible in each of these figures.
Figure 8B:
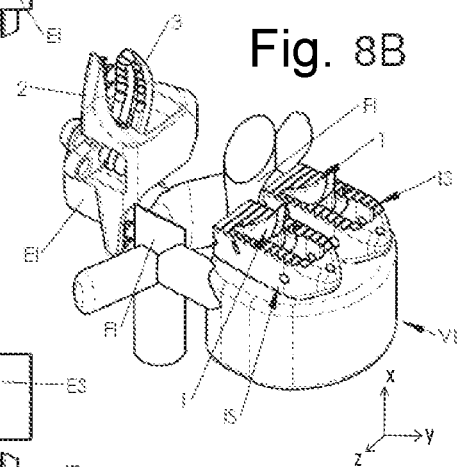
Figure 8C:
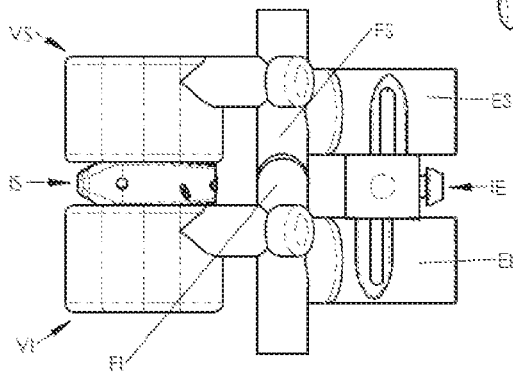
Figure 8D:
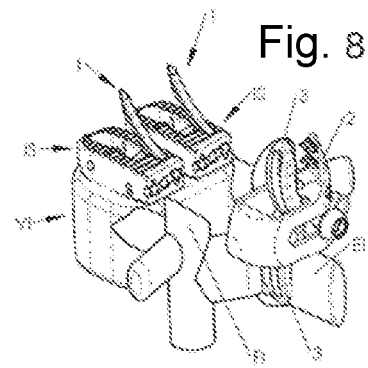
Figure 8E:
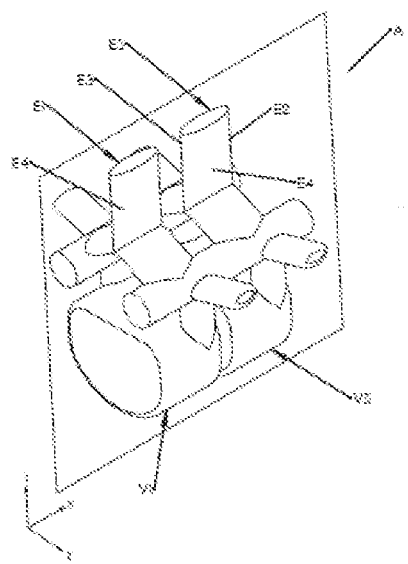
FIG. 8E represents a perspective view oriented towards opposite side faces of two adjacent vertebrae of the rachis, illustrating the vertebral spines, the sagittal plane of the rachis and a three-dimensional reference system used as a reference.
Figure 9A:
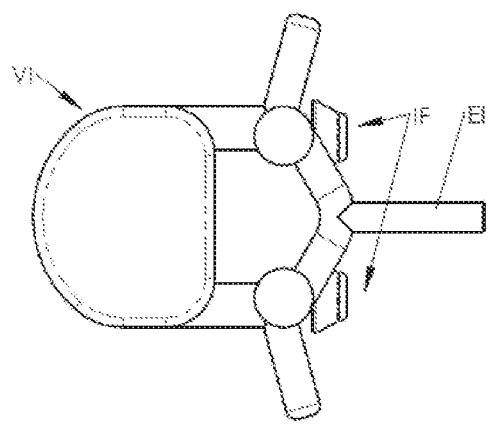
FIGS. 9A, 9B, 9C and 9D respectively represent underside, front perspective, profile and rear perspective views of an arthrodesis system according to an embodiment comprising two intersomatic implants and two facet implants for the arthrodesis of two adjacent vertebrae, at least one of which is visible in each of these figures.
Figure 9B:
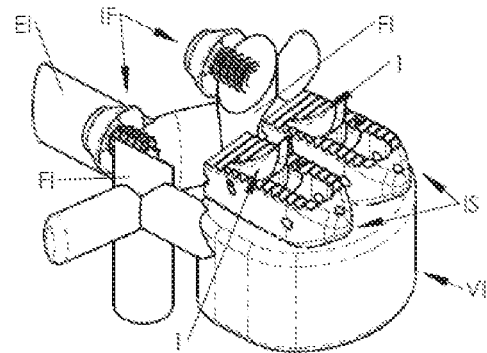
Figure 9C:
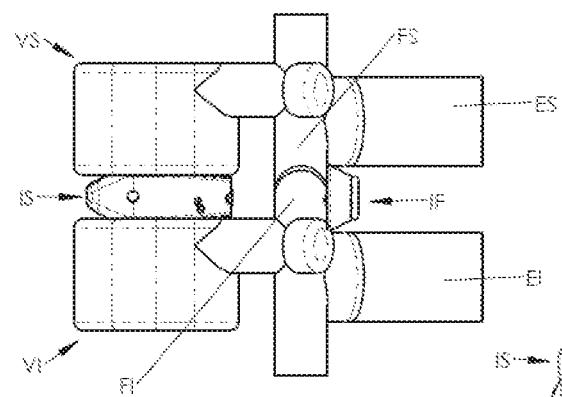
Figure 9D:
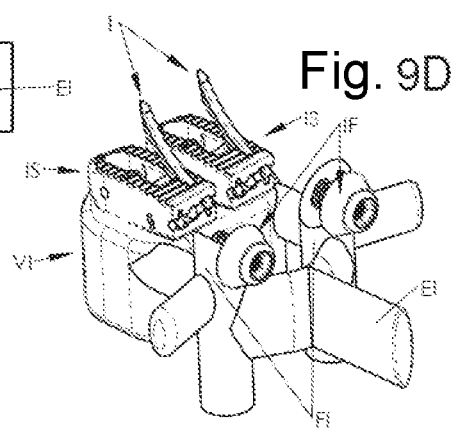
Figure 10A:
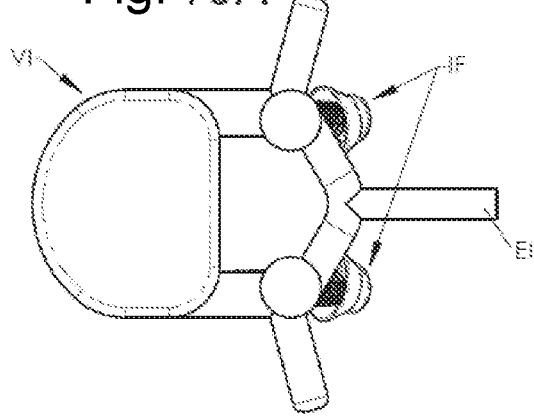
FIGS. 10A, 10B, 10C, 10D and 10E respectively represent underside, front perspective, profile, rear perspective and top views, of an arthrodesis system according to an embodiment comprising two intersomatic implants and two transfacet implants, for the arthrodesis of two adjacent vertebrae, at least one of which is visible in each of these figures.
Figure 10B:
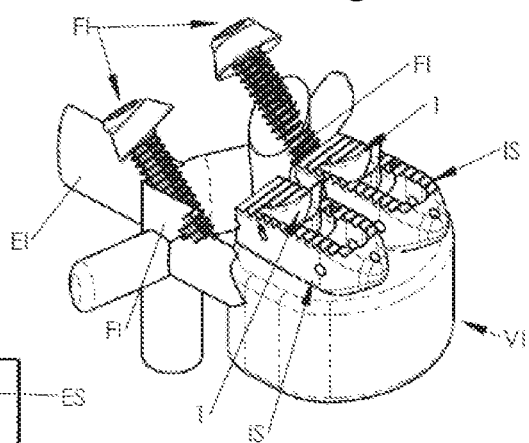
Figure 10C:
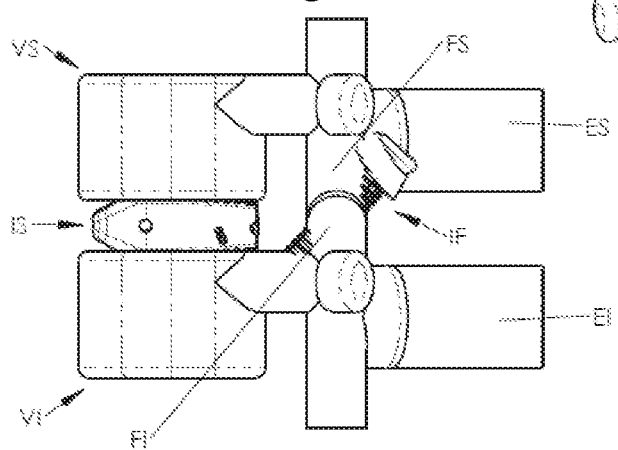
Figure 10D:
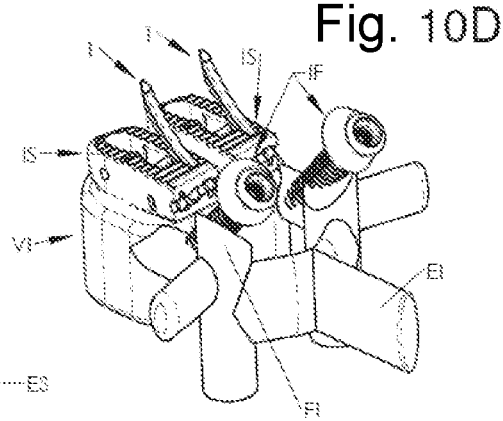
Figure 10E:
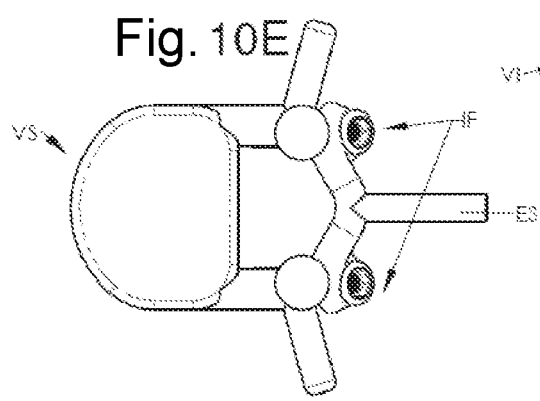

FIG. 8E schematically illustrates perspective views of the constitutive elements of two adjacent vertebrae (VI, VS) with the median sagittal plane (A) and a Cartesian reference system (X, Y, Z) which are used as references in the present description for the sake of simplification. These figures illustrate a lower vertebra (VI) with its spine, a so-called also lower spine (EI), and an upper vertebra (VS) with its spine also a so-called upper spine (ES) and show the edges (E2, E3) and faces (E4, E5) of each of these upper (ES) and lower (EI) spines. The present application describes certain elements of the implant with reference to its positioning once it is implanted in the body of the patient, for more clarity on the localization of the diverse elements of the implant with respect to the vertebral structures. In FIG. 8E, the patient is considered to be in a horizontal position, lying face-down. The illustrated Cartesian reference system includes three orthogonal directions (X, Y, Z) to each other. The direction X corresponds to the ascending longitudinal axis of the rachis, the direction Y corresponds to the anteroposterior axis and the direction Z corresponds to the mediolateral axis. Thus, the axes X and Y define a sagittal plane (A) the axes X and Z define a coronal plane and the axes Y and Z define a transverse plane of the patient. The present application may refer to these planes of the patient for the actual implant. The terms of "upper" and "lower" are therefore used in the present application with reference to the axis X. A top view is a view according to which the rachis or the implant is observed from the rear of the patient lying face down and a side view is a view according to which the rachis or the implant is observed from a side face of the rachis or of the implant according to this same reference. These considerations of views and orientations are used independently of whether the implant is implanted or not and it will be understood that they relate to the implant in its implantation destination but they are not limiting. Further, it will also be understood from the present application that the implant may be turned over along the side face of the rachis from which the surgeon wishes to approach the inter-spinous space. On the other hand, it will be understood that the invention gives the possibility of approaching the spines through a single lateral face of the rachis but that the approach preferably is performed perpendicularly to the sagittal plane (along the Z axis) but rather substantially parallel to the Y axis or preferably along an oblique axis which is oriented towards the rear of the patient (an axis oriented between the axes Y and Z, but also possibly not parallel with the X axis if required).

On the other hand, it will be understood that the insertions of the implant and of the insert are preferably carried out substantially parallel to the Z axis. Finally, always with reference to these markings on the patient, in the present application, the terms of "height" (notably of the implant) or "length" (notably of the wings or of the insert) are used for referring to a dimension along the X direction, the terms of "width" (notably of the implant) or "thickness" (notably of the wings or of the insert) for referring to a dimension along the Z direction and the term of "depth" for referring to a dimension along the Y axis. These terms used for the dimensions along the axes and directions of the reference system are not limiting and do not mean that the relevant elements are necessarily oriented exactly along the axis to which reference is made and this reference may concern their orthogonal projection on the axis or their dimension along an axis approximately oriented in the same direction as the axis to which reference is made. The present invention relates to an interspinous implant (IE) intended to be implanted between two vertebral spines (EI, ES) of said vertebrae (VI, VS), the interspinous implant including at least two wings (21, 22, 31, 34) of dimensions laid out so as to be inserted between vertebral spines (EI, ES) of said adjacent vertebrae (VI, VS), from one of their side faces.

The term of "wing" in the present application refers to an element of the implant (IE) which extends towards the side faces of the spines (generally longitudinally and substantially parallel to the axis X of the rachis) and should not be interpreted in a limiting way since the wings may have diverse shapes, diverse examples of which are detailed in the present application. It will be noted in particular that the wings are in fact extensions of the body (for example on the side faces or on the upper and lower faces, or rather at the junction between these faces). Certain wings are jointed and included in a locking mechanism for the jointing so as to fulfill their function of retaining the implant and generally allowing a compression means to be provided advantageously. Generally, the wings (which may be called arms, legs, extension or other term) may be in the form of a straight or curved plate and will preferably have shapes and dimensions adapted to proper maintaining of the implant between the spines. For example in the case of curved wings, the insertion of the implant will be facilitated and the free end of the curved wings will be found closer to the size faces of the spines than the remainder of the implant, or even in contact with these side faces for allowing proper maintaining of the implant between the spines. The dimensions of the wings may also be adapted to the dimensions of the side faces of the spines. For example, the wings may have a length (substantially parallel to the axis X of the rachis), of the order of half of that of the side faces of the spines, or even greater (which will be particularly advantageous for providing good maintaining, and it will even be possible in certain embodiments where the wings have arranged shapes for allowing implantation of several implants in the successive interspinous spaces of several successive vertebrae of the rachis, for example as detailed in the present application). The depth of the implant in a general way may vary depending on the size of the spines along an axis substantially parallel to the Y axis of the rachis and/or according to the wish of the surgeon, in order to provide a more or less significant maintaining of the spines, by a contact with a more or less extended surface on the upper and lower edges of the spines. This depth may also be determined depending on total desired size of the implant, in order to minimize the lesions required at its implantation. Thus, the implant may have a thereby determined depth and the wings (31, 32) may have a substantially identical or different depth, according to the needs defined by the surgeon. Further, the term of "wing" is used here for referring to a structure protruding from an edge or an angle of the body of the implant and which extends so that the dimensions of the implant prevent the wings from freely passing between both spinouses by a simple translation along an axis parallel to the Z axis, at least when the wings are deployable. But as described above, in the case of partial resection of the spinouses, it is also conceivable to have fixed wings and an implantation of the interspinous implant by translation along an axis parallel to the Y axis. The term of "wing" should not be considered as limiting. Further, reference is made in the present application to least two deployable wings and it is therefore possible to provide four deployable wings or two fixed wings and two deployable wings, but also only two fixed wings, notably when the interspinous implant is provided with immobilization means, for example as descried hereafter. Finally, the terms of "deploy or deployable or deployment" designate in the present application both a pivoting, such as for example illustrated in a non-limiting way in FIGS. 3A to 3C of the present application, and a translation of an insert, such as for example illustrated in a non-limiting way in FIGS. 1, 4 and 6 of the prior art application US 2005/203512, or a combination of both.

In certain embodiments, said interspinous implants (IE) comprise immobilization means so as to immobilize the vertebral structure in which it is configured for being implanted.

In certain embodiments, said immobilization means are means for hooking-up a spinous laid out for hooking-up around at least one portion of the edge of a spine which is opposite to the edge of this spine against which the body of the implant is affixed. Said spinous hooking-up means includes at least one pivotally mount hook on the body of the implant and laid out so as to be hooked-up around a spine, at at least one portion of the edge which is opposite to the edge against which the body of the implant is affixed. Said hooking-up means is described in application WO 2013/001097 and illustrated in a non-limiting way in FIGS. 20 to 23 of said application. In this type of embodiment, the interspinous implant, implanted in the interspinous space, is attached around the spines and immobilized, which facilitates fusion.

In certain embodiments, said immobilization means are attachment means. Said attachment means may be elements penetrating into dorsal spines, notably, such as a screw or a nail or at least one plate. In the case of a nail or plate, it is preferred that they be curved for limiting the risks of movement. Said attachment means may also be elements surrounding the dorsal spines so as to immobilize said spines, such as a ligament for example. This type of embodiment therefore also allows immobilization of the interspinous implant in the interspinous space and facilitates bone fusion.

In certain embodiments, said immobilization means are means for compressing the side faces of at least one spinous. Preferably, a compression of the spinouses is provided by pivoting of at least one wing of the implant or of an insert of the implant for pressing the spinous between this pivoting wing and at least one other fixed or also pivoting wing. This type of embodiment comprising a means for compressing the spinouses (for example and in particular by applying pressure on the side faces) gives the possibility of stabilizing the interspinous implant in the interspinous space and facilitate bone fusion.

In certain embodiments, the system includes at least one interspinous implant (IE), including at least one body (2) of laid out dimensions so as to be inserted between two vertebral spines (EI, ES) of said adjacent vertebrae (VI, VS), from one of their side faces, and including at least two wings (21, 22) on the one hand extending non-parallel to the body (2) so that at least one portion of each wing (21, 22) runs along at least one side portion of one of the two spines (EI, ES) and at least one passage (28) crossing said body (2) from one side face to the other on the other hand and receiving at least one means for retaining the interspinous implant (IE), formed by an insert (3), inserted from the same side face of the implant and comprising at least one curved and rigid wing (31, 32) sliding in said passage (28) without any deformation until at least one portion of said curved and rigid wings (3) (31, 32) protrudes on the outside of said passage (28) and runs along at least one portion of a side face opposite to the one bordered by a wing (21, 22) of the implant. The insert comprises at least one curved and rigid wing with a shape of rectangular, circular, square, polygonal or T-shaped, L-shaped, U-shaped or even H-shaped section. Various embodiments of the interspinous implant have a longitudinal body (2) including at least two wings (21, 22) positioned on a same side face of the implant (IE) for running along both spines (EI, ES) on the same side face, said passage (28) crossing the implant from this same side face as far as the side face for inserting an insert (3) comprising two curved wings (31, 32) each protruding towards one of the spines (EI, ES) for running along the same opposite side face, so that the implantation of the implant and of the insert (3) between the spines (EI, ES) may be carried out from a single side face.

According to an embodiment of the present invention, the implant (IE) includes two wings (21, 22) each positioned on a side face of the implant opposite to the other wing and each protruding towards one of the two spines, so that the wings each run along a spine (EI, ES) but on opposite side faces (E4, E5), the insert (3) being of a substantially sigmoidal shape by the fact that its body includes at least two radii of curvature with opposite orientations, so that two faces of said body each include a concave portion and a convex portion, the passage (28) and the insert (3) being laid out so that when the insert (3) is housed in the passage (28) at least one portion of said convex portions of both faces of the insert (3) each run along at least one portion of the spines (EI, ES), on side faces opposite to those bordered by the wings (21, 22).

In another embodiment, the interspinous implant (IE) includes compressing means (31, 32, 35) for compressing the side faces of the spinouses (EI, ES) between said wings (21, 22) and said insert (3) when the latter is inserted through said passage (28) of the interspinous implant (IE). Said compression means are formed by two curved wings (31, 32) of the insert (3) connected through a joint axis (35) allowing the deployment of both bodies from a folded back position during the insertion of the insert (3) into the passage (28) at a deployed position wherein said wings (31, 32) compress the spinouses against the wings (21, 22) of the implant (IE).

Figure 3A:
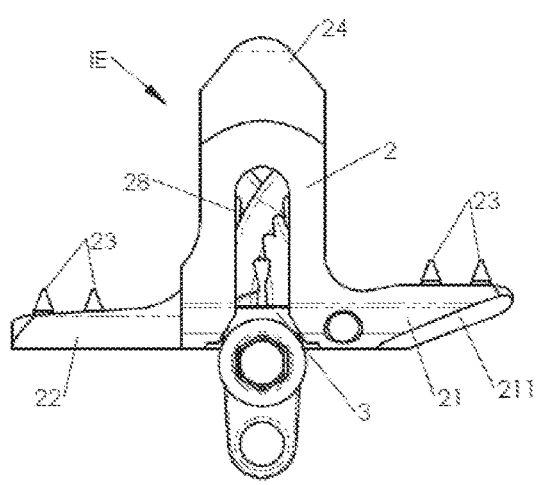
FIGS. 3A, 3B and 3C represent top views of an insert for an interspinous implant according to an embodiment, respectively during insertion, during deployment and after deployment of a deployable insert in the interspinous implant.
Figure 3B:
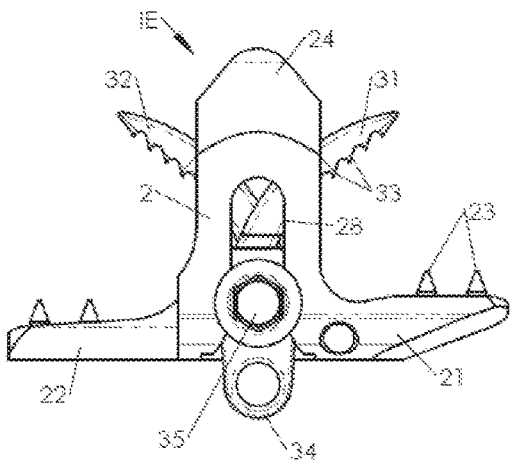
Figure 3C:
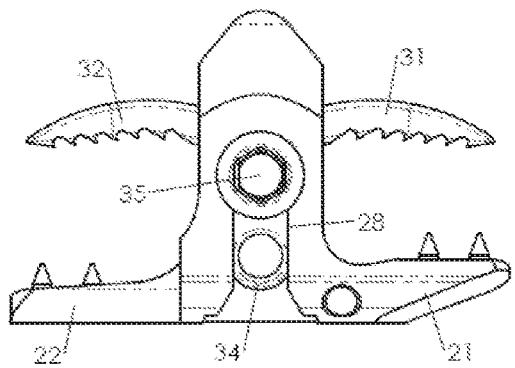
Figure 3D:
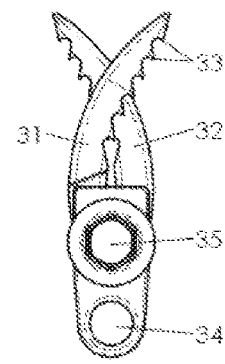
FIG. 3D represents a top view of an insert for an interspinous implant, in the folded back position
Figure 3E:
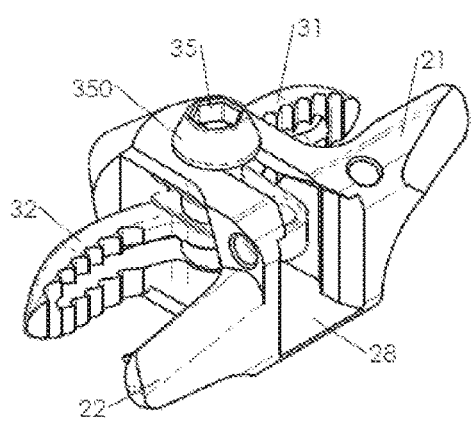
FIG. 3E represents a perspective view of an interspinous implant provided with its deployed insert.

As illustrated in FIGS. 3C, 3D and 3E, said wings (31, 32) of the insert (3) are connected through a joint providing a compression means at their posterior end and allowing the deployment of two wings (31, 32) from a folded back position wherein the wings are in contact or close to each other, as illustrated in FIGS. 3A and 3D, to a deployed position wherein the wings are separated from each other as illustrated in FIGS. 3C and 3E. The deployment of both wings (31, 32) takes place, in these embodiments, by means of this joint and in contact of the wings with the bottom of the passage (28) (i.e., at least one wall located in the passage axis and opposite to the inlet of the latter) and the deployment degree (i.e., the orientation of the inserts in a deployed position) therefore depend on the position of the joint in the passage. Such a means for compressing the joint preferably forms a joint axis (35) on which are mounted free to rotate, the posterior ends of the wings (31, 32) of the insert (3), for example by means of eyelids (34) formed at these posterior ends. The joint axis (250), for example formed by a rod, a screw, a rivet or any other structure may, at a first end form an abutment for retaining one of the wings (31 or 32) in translation along the axis (250), the other wing (31 or 32) then also being retained by its intertwining with the first.

In certain embodiments, the interspinous implant (IE) includes at least two wings (31, 32) extending so that at least one portion of each wing (31, 32) runs along at least one portion of a side face of one of the two spines (EI, ES) on the one hand and at least one passage (28) at least crossing through a portion of the body (2), on the other hand. In various embodiments, this passage has a shape, dimensions and an orientation laid out for inserting, through the body (2) at least one insert (3). In various embodiments, the inset (3) comprises at least one curved wing retained in the body (2) so that at least one portion of said curved wing runs along at least a portion of a side face opposite to (at least) one side face bordered by a wing (31, 32) (one side face or two side faces as detailed in said embodiment). It is understood that at least one implant provided with at least one wing running along a side face of a spine, the other side face of which is bordered by a portion of at least one insert forming at least one other wing deployed through a passage of the implant, is thereby obtained. In these embodiments, this configuration therefore allows insertion of the implant from a side face facing which will be positioned a wing and then insertion into the passage (28) of the implant, through the same side face, an insert (3), a curved portion of which gives the possibility of facing the opposite side face (located on the other side of the spine and to which one therefore has no direct access) and potentially another curved portion on the side from which the insert is inserted.

According to an embodiment, the insert (3) is retained in the implant, even if it is attached thereto. Abutment means are described in the present applications as examples of an abutment (or attachment) mechanism of the insert. However, in certain embodiments, the insert (3) is retained in the implant without any abutment means. For example, in certain embodiments, the insert (3) may be retained in the implant by means of a thickened portion of the insert which will come into contact with the walls in the passage of the implant, so that the insert is driven in by force into the passage and is maintained therein by friction. Also, rather than a thickening, it is possible that the insert be retained in the implant by the fact that its curvature is so large with respect to the dimensions of the passage that it has to be forced into the latter and is found held therein by its contact with the walls of the passage. A not very flexible insert will then be preferred for avoiding that it may too easily be detached from the passage by deforming under the effect of stresses. Nevertheless, in order to ensure proper retention of the insert, various abutment mechanisms comprising specific abutment means are also contemplated.

In certain embodiments, in particular those wherein the implant (IE) includes two wings on the same side face, the body preferably includes, but in a non-limiting way, on its anterior portion (intended to be inserted first), at least one chamfer (24) for facilitating its insertion into the interspinous space (in particular through the interspinous ligament). For example, as particularly visible in FIGS. 3A and 3B, the body may be provided with chamfers (24) at the anterior end of the upper and lower faces, but also with faces positioned in the direction of the front and of the rear of the patient.

In certain embodiments not shown, means for hooking-up a spinous (EI, ES), not shown in the figures, are provided for improving the retention of the implant between both spines, by hooking-up at least one of the two adjacent spines between which the implant is positioned and they then provide a function for retaining the spinouses in addition to the function of retaining the implant. By "hooking-up means" are meant here means which are laid out so as to hook up around at least one portion of the edges of the spines which are opposite to the edges of the spines between which the implant is inserted.

The present application describes various technical features and advantages with reference to the figures and/or to various embodiments. One skilled in the art will understand that the technical features of a given embodiment may in fact be combined with features of another embodiment unless the opposite is explicitly mentioned or if it is obvious that these features are incompatible and that the combination does not provide a solution to at least one of the technical problems mentioned in the present application. Further, the technical features described in a given embodiment may be isolated from the other features of this embodiment unless the opposite is explicitly mentioned.

It should be obvious for persons skilled in the art that the present invention allows embodiments in many other specific forms without departing from the field of application of the invention as claimed. Therefore, the present embodiments have to be considered as an illustration, but may be modified in the field defined by the scope of the appended claims, and the invention should not be limited to the details given above.

The invention claimed is:

1. A system for arthrodesis of a first vertebra and a second vertebra adjacent to the first vertebra comprising:
   an intersomatic cage and a cage anchor;
   an interspinous implant comprising a body, a plurality of foldable wings movable with respect to the body and an insert coupled to one end of each foldable wing of the plurality of foldable wings, the insert linearly advanceable within the body to extend the plurality of foldable wings from a storage position within the body to a deployed position outside the body; and
   a facet screw having a longitudinal axis between a free end and a head, the screw comprising an internal conduit along at least a portion of the longitudinal axis and a plurality of windows extending from an exterior surface of the screw into the conduit.

2. The system of claim 1 in which a tapered bell is disposed at the head of the facet screw, with a first diameter of the bell oriented toward the head of the facet screw and a second diameter of the bell oriented toward the free end of the facet screw, and with the first diameter being smaller than the second diameter.

3. The system of claim 1 in which a staple is disposed at the head of the facet screw, with sharpened ends of the staple oriented toward the free end of the facet screw.

4. The system of claim 1 wherein the interspinous implant includes a plurality of stationary wings attached to the body opposite the plurality of foldable wings movable with respect to the body.

5. The system of claim 4, wherein the plurality of stationary wings includes a first stationary wing attached to the body and positioned to receive a first side of a first spinous process upon implantation, and a second stationary wing attached to the body and positioned to receive a first side of a second spinous process.

6. The system of claim 1, wherein the cage anchor is a curved anchor.

7. The system of claim 6, wherein the intersomatic cage includes a first passage positioned to be accessible from outside the intervertebral space after insertion of the intersomatic cage.

8. The system of claim 7, wherein the first passage is curved to enable insertion of the curved anchor.

9. The system of claim 8, wherein the first passage extends from an end surface of the intersomatic cage to a superior or inferior surface to direct the curved anchor into a superior or inferior vertebral endplate upon implantation.

10. The system of claim 1, wherein the plurality of foldable wings are pivotably coupled to the insert.

11. The system of claim 10, wherein the insert includes a joint axis where the plurality of foldable wings are pivotably coupled to the insert.

12. The system of claim 11, wherein the joint axis includes a compression member to maintain the plurality of foldable wings in a deployed position.

13. The system of claim 12, wherein the compression member is formed from a screw extending through the joint axis.

14. A method for arthrodesis of a first vertebra and a second vertebra adjacent to the first vertebra comprising the steps of:
- placing a cage in an intervertebral space between the first vertebra and the second vertebra;
- inserting a curved anchor through a first passage in the cage accessible from outside the intervertebral space;
- fixing the cage to the first vertebra by advancing the anchor in the first passage until a tip of the anchor emerges from the first passage in the cage and enters into the first vertebra;
- inserting an interspinous implant body between a first spinous process of the first vertebra and a second spinous process of the second vertebra;
- inserting an interspinous implant insert into a second passage in the interspinous implant body;
- fixing the first spinous process and the second spinous process by
- advancing the interspinous implant insert in the second passage until a first stationary wing attached to the implant body is against a first side of the first spinous process, a second stationary wing attached to the implant body is against a first side of the second spinous process, a first foldable wing attached to the interspinous implant insert is against a second side of the first spinous process, and a second foldable wing attached to the interspinous implant insert is against a second side of the second spinous process,
- compressing the first stationary wing and the first foldable wing against the first spinous process, and
- compressing the second stationary wing and the second foldable wing against the second spinous process; and
- fixing a first articular facet of the first vertebra and a second articular facet of the second vertebra with a facet screw.

* * * * *